(12) United States Patent
Fuchigami et al.

(10) Patent No.: US 12,374,002 B2
(45) Date of Patent: Jul. 29, 2025

(54) IMAGE PROCESSING APPARATUS, METHOD AND PROGRAM, LEARNING APPARATUS, METHOD AND PROGRAM, AND DERIVATION MODEL

(71) Applicant: FUJIFILM Corporation, Tokyo (JP)

(72) Inventors: Takuya Fuchigami, Tokyo (JP); Sadato Akahori, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 399 days.

(21) Appl. No.: 17/938,045

(22) Filed: Oct. 4, 2022

(65) Prior Publication Data

US 2023/0022549 A1 Jan. 26, 2023

Related U.S. Application Data

(63) Continuation of application No. PCT/JP2021/014212, filed on Apr. 1, 2021.

(30) Foreign Application Priority Data

Apr. 9, 2020 (JP) ................................. 2020-070312
Nov. 9, 2020 (JP) ................................. 2020-186787

(51) Int. Cl.
| | | |
|---|---|---|
| *G06T 7/12* | (2017.01) | |
| *G06T 7/00* | (2017.01) | |
| *G06T 7/33* | (2017.01) | |
| *G06T 11/00* | (2006.01) | |
| *G06V 10/778* | (2022.01) | |

(52) U.S. Cl.
CPC .......... *G06T 11/003* (2013.01); *G06T 7/0016* (2013.01); *G06T 7/337* (2017.01);
(Continued)

(58) Field of Classification Search
CPC ..... G06T 11/003; G06T 7/0016; G06T 7/337; G06T 2207/10081; G06T 2207/20081;
(Continued)

(56) References Cited

U.S. PATENT DOCUMENTS 8,165,372 B2 * 4/2012 Ishikawa .............. A61B 8/4254
382/128
9,746,535 B2 * 8/2017 Nitta .................. G01R 33/4835
(Continued)

FOREIGN PATENT DOCUMENTS

| | | |
|---|---|---|
| JP | 2004283483 | 10/2004 |
| JP | 2013102889 | 5/2013 |
| JP | 2016527994 | 9/2016 |

OTHER PUBLICATIONS

"Office Action of Japan Counterpart Application", issued on Aug. 15, 2023, with English translation thereof, p. 1-p. 6.
(Continued)

*Primary Examiner* — Stephen R Koziol
*Assistant Examiner* — Dylan J Sherrillo
(74) *Attorney, Agent, or Firm* — JCIPRNET

(57) ABSTRACT

An image processing apparatus includes at least one processor, and the processor derives three-dimensional coordinate information that defines a position of a structure in a tomographic plane from a tomographic image including the structure, and that defines a position of an end part of the structure outside the tomographic plane in a direction intersecting the tomographic image.

16 Claims, 15 Drawing Sheets

(52) U.S. Cl.
CPC .............. *G06V 10/7784* (2022.01); *G06T 2207/10081* (2013.01); *G06T 2207/20081* (2013.01); *G06T 2207/30004* (2013.01); *G06T 2210/12* (2013.01)

(58) Field of Classification Search
CPC ....... G06T 2207/30004; G06T 2210/12; G06T 2207/10072; G06T 2207/20084; G06T 2207/20132; G06T 7/12; G06T 1/00; G06T 3/00; G06V 10/7784; A61B 5/055; A61B 6/00; A61B 6/03; G01T 1/161; G06N 3/08; G06N 20/00
See application file for complete search history.

(56) References Cited

U.S. PATENT DOCUMENTS

| | | | |
|---|---|---|---|
| 11,551,353 B2* | 1/2023 | Golden | G06V 10/82 |
| 2013/0154646 A1 | 6/2013 | Nitta et al. | |
| 2015/0049081 A1 | 2/2015 | Coffey et al. | |
| 2015/0049082 A1 | 2/2015 | Coffey et al. | |
| 2015/0049083 A1 | 2/2015 | Bidne et al. | |
| 2016/0238682 A1 | 8/2016 | Nitta et al. | |
| 2018/0122150 A1 | 5/2018 | Bidne et al. | |
| 2018/0137690 A1 | 5/2018 | Coffey et al. | |
| 2018/0315188 A1* | 11/2018 | Tegzes | G06T 7/11 |
| 2019/0050981 A1 | 2/2019 | Song et al. | |
| 2021/0133977 A1* | 5/2021 | Yamazaki | G06V 10/82 |

OTHER PUBLICATIONS

"International Search Report (Form PCT/ISA/210) of PCT/JP2021/014212," mailed on Jun. 8, 2021, with English translation thereof, pp. 1-5.

"Written Opinion of the International Searching Authority (Form PCT/ISA/237)" of PCT/JP2021/014212, mailed on Jun. 8, 2021, with English translation thereof, pp. 1-8.

* cited by examiner

IMAGE PROCESSING APPARATUS, METHOD AND PROGRAM, LEARNING APPARATUS, METHOD AND PROGRAM, AND DERIVATION MODEL

CROSS REFERENCE TO RELATED APPLICATIONS

The present application is a Continuation of PCT International Application No. PCT/JP2021/014212, filed on Apr. 1, 2021, which claims priority to Japanese Patent Application No. 2020-070312, filed on Apr. 9, 2020, and Japanese Patent Application No. 2020-186787, filed on Nov. 9, 2020. Each application above is hereby expressly incorporated by reference, in its entirety, into the present application.

BACKGROUND

Technical Field

The present disclosure relates to an image processing apparatus, method and program, a learning apparatus, method and program, and derivation model for three-dimensional images.

Related Art

In recent years, advances in medical devices, such as computed tomography (CT) apparatuses and magnetic resonance imaging (MRI) apparatuses, have enabled image diagnosis using high-resolution medical images with higher quality. In particular, since a region of a lesion can be accurately specified by image diagnosis using three-dimensional images such as CT images and MRI images, appropriate treatment is being performed based on the specified result.

Incidentally, in order to extract a structure such as an organ included in a three-dimensional image, it has been proposed to set a rectangular cuboid (that is, a bounding box) indicating the range of a structure in the three-dimensional image. For example, JP2016-527994A proposes a method of generating an intermediate three-dimensional representation at a position identified in one tomographic image of a three-dimensional image, and generating a three-dimensional model of a structure from the intermediate three-dimensional representation to thereby draw a bounding box indicating the range of the three-dimensional model.

However, the process of setting three-dimensional coordinates of the bounding box indicating the range of the structure in the three-dimensional image requires a long time because the amount of calculation is large.

SUMMARY OF THE INVENTION

The present disclosure has been made in view of the above circumstances, and an object of the present disclosure is to efficiently set three-dimensional coordinates indicating the range of a structure in a three-dimensional image.

According to an aspect of the present disclosure, there is provided an image processing apparatus comprising at least one processor, in which the processor is configured to derive three-dimensional coordinate information that defines a position of a structure in a tomographic plane from a tomographic image including the structure, and that defines a position of an end part of the structure outside the tomographic plane in a direction intersecting the tomographic image.

In the image processing apparatus according to the aspect of the present disclosure, the processor may be configured to select at least one tomographic image including the structure from a three-dimensional image including a plurality of tomographic images.

Further, in the image processing apparatus according to the aspect of the present disclosure, the three-dimensional coordinate information may include three-dimensional coordinates of a plurality of vertices defining a rectangular cuboid surrounding the structure.

Further, in the image processing apparatus according to the aspect of the present disclosure, the plurality of vertices may include two vertices at the farthest positions among the vertices defining the rectangular cuboid.

The wording "include the two vertices at the farthest positions" means that not only the two vertices at the farthest positions but also other vertices other than the two vertices may be included.

Further, in the image processing apparatus according to the aspect of the present disclosure, the processor may be configured to derive the three-dimensional coordinate information by deriving provisional three-dimensional coordinate information about the structure from each of a plurality of tomographic images including the common structure, and integrating the provisional three-dimensional coordinate information.

In this case, the processor may be configured to derive the three-dimensional coordinate information may be derived by converting the provisional three-dimensional coordinate information for each of the plurality of tomographic images into a common coordinate system, and integrating the converted provisional three-dimensional coordinate information.

Further, in this case, the processor may be configured to derive the three-dimensional coordinate information by integrating the provisional three-dimensional coordinate information closer to an upper end or a lower end of the same structure with high priority with respect to the provisional three-dimensional coordinate information derived for the tomographic image including the upper end or the lower end.

The wording "integrating" means deriving one piece of three-dimensional coordinate information from a plurality of pieces of provisional three-dimensional coordinate information. For example, as "integration", arithmetic mean, weighted arithmetic mean, and the like can be used.

Further, in the image processing apparatus according to the aspect of the present disclosure, the processor may be configured to acquire a first three-dimensional image and a second three-dimensional image each including a plurality of tomographic images and the common structure, derive first three-dimensional coordinate information about the structure included in the first three-dimensional image and second three-dimensional coordinate information about the structure included in the second three-dimensional image, and align the first three-dimensional image and the second three-dimensional image at least in the direction intersecting the tomographic image by using the first three-dimensional coordinate information and the second three-dimensional coordinate information to align the common structure included in each of the first three-dimensional image and the second three-dimensional image at least in the direction intersecting the tomographic image.

In this case, the first three-dimensional image and the second three-dimensional image may be three-dimensional images of the same subject imaged with different imaging apparatuses.

Further, in this case, the first three-dimensional image and the second three-dimensional image may be three-dimensional images of the same subject imaged at different imaging times.

Further, in this case, the processor may be configured to derive the first and second three-dimensional coordinate information for each of the first and second three-dimensional images by different methods.

Further, the image processing apparatus according to the aspect of the present disclosure may further comprise a derivation model trained using supervised training data to output the three-dimensional coordinate information that, in a case where the tomographic image is input, defines the position of the structure included in the input tomographic image in the tomographic plane, and that defines the position of the end part of the structure outside the tomographic plane in the direction intersecting the tomographic image.

According to another aspect of the present disclosure, there is provided a learning apparatus comprising at least one processor, in which the processor is configured to construct a derivation model by performing machine learning using supervised training data, the derivation model outputting three-dimensional coordinate information that, in a case where a tomographic image is input, defines a position of a structure included in the input tomographic image in a tomographic plane, and that defines a position of an end part of the structure outside the tomographic plane in a direction intersecting the tomographic image.

Further, in the learning apparatus according to the aspect of the present disclosure, the supervised training data may include a supervised training tomographic image and supervised training three-dimensional coordinate information that defines a position of the structure included in the supervised training tomographic image in the tomographic plane, and that defines a position of the end part of the structure outside the tomographic plane in a direction intersecting the supervised training tomographic image.

According to still another aspect of the present disclosure, there is provided a derivation model that is constructed by performing machine learning using supervised training data to output three-dimensional coordinate information that, in a case where a tomographic image is input, defines a position of a structure included in the input tomographic image in a tomographic plane, and that defines a position of an end part of the structure outside the tomographic plane in a direction intersecting the tomographic image.

According to still another aspect of the present disclosure, there is provided an image processing method comprising deriving three-dimensional coordinate information that defines a position of a structure in a tomographic plane from a tomographic image including the structure, and that defines a position of an end part of the structure outside the tomographic plane in a direction intersecting the tomographic image.

According to still another aspect of the present disclosure, there is provided a learning method comprising constructing a derivation model by performing machine learning using supervised training data, the derivation model outputting three-dimensional coordinate information that, in a case where a tomographic image is input, defines a position of a structure included in the input tomographic image in a tomographic plane, and that defines a position of an end part of the structure outside the tomographic plane in a direction intersecting the tomographic image.

In addition, the image processing method and the learning method according to the aspects of the present disclosure may be provided as a program for causing a computer to execute the methods.

According to the aspects of the present disclosure, it is possible to efficiently set the three-dimensional coordinates indicating the range of the structure in the three-dimensional image.

DETAILED DESCRIPTION

Hereinafter, an embodiment of the present disclosure will be described with reference to the drawings. First, a configuration of a medical information system 1 to which an image processing apparatus and a learning apparatus according to the present embodiment are applied will be described.

Figure 1:
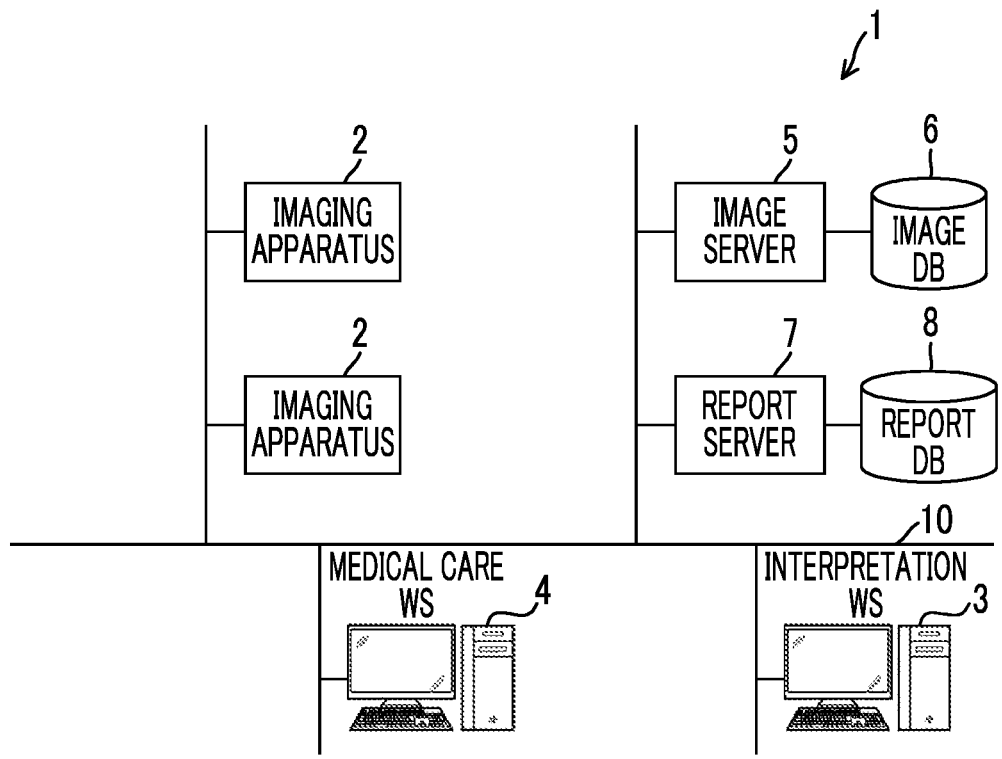
FIG. 1 is a diagram showing a schematic configuration of a medical information system to which an image processing apparatus and a learning apparatus according to an embodiment of the present disclosure are applied.

FIG. 1 is a diagram showing a schematic configuration of the medical information system 1. The medical information system 1 shown in FIG. 1 is, based on an examination order from a doctor in a medical department using a known ordering system, a system for imaging an examination target part of a subject, storing a medical image acquired by the imaging, interpreting the medical image by a radiologist and creating an interpretation report, and viewing the interpretation report and observing the medical image to be interpreted in detail by the doctor in the medical department that is a request source.

As shown in FIG. 1, in the medical information system 1, a plurality of imaging apparatuses 2, a plurality of interpretation workstations (WSs) 3 that are interpretation terminals, a medical care WS 4, an image server 5, an image database (hereinafter referred to as an image DB) 6, a report server 7, and a report database (hereinafter referred to as a report DB) 8 are communicably connected to each other through a wired or wireless network 10.

Each apparatus is a computer on which an application program for causing each apparatus to function as a component of the medical information system 1 is installed. The application program is stored in a storage apparatus of a server computer connected to the network 10 or in a network storage in a state in which it can be accessed from the outside, and is downloaded to and installed on the computer in response to a request. Alternatively, the application program is recorded on a recording medium, such as a digital versatile disc (DVD) and a compact disc read only memory (CD-ROM), and distributed, and is installed on the computer from the recording medium.

The imaging apparatus 2 is an apparatus (modality) that generates a medical image showing a diagnosis target part of the subject by imaging the diagnosis target part. Specifically, examples of the modality include a simple X-ray imaging apparatus, a CT apparatus, an MRI apparatus, a positron emission tomography (PET) apparatus, and the like. In the present embodiment, it is assumed that the imaging apparatus 2 acquires a three-dimensional image consisting of a plurality of slice images as a medical image. The medical image generated by the imaging apparatus 2 is transmitted to the image server 5 and is saved in the image DB 6.

The interpretation WS 3 is a computer used by, for example, a radiologist of a radiology department to interpret a medical image and to create an interpretation report, and encompasses an image processing apparatus and a learning apparatus according to the present embodiment. In the interpretation WS 3, a viewing request for a medical image to the image server 5, various image processing for the medical image received from the image server 5, display of the medical image, input reception of comments on findings regarding the medical image, and the like are performed. In the interpretation WS 3, interpretation of medical images, creation of an interpretation report based on the interpretation result, a registration request and a viewing request for the interpretation report to the report server 7, and display of the interpretation report received from the report server 7 are performed. The above processes are performed by the interpretation WS 3 executing software programs for respective processes.

The medical care WS 4 is a computer used by a doctor in a medical department to observe an image in detail, view an interpretation report, create an electronic medical record, and the like, and is configured to include a processing apparatus, a display apparatus such as a display, and an input apparatus such as a keyboard and a mouse. In the medical care WS 4, a viewing request for the image to the image server 5, display of the image received from the image server 5, a viewing request for the interpretation report to the report server 7, and display of the interpretation report received from the report server 7 are performed. The above processes are performed by the medical care WS 4 executing software programs for respective processes.

The image server 5 is a general-purpose computer on which a software program that provides a function of a database management system (DBMS) is installed. The image server 5 comprises a storage in which the image DB 6 is configured. The storage may be a hard disk apparatus connected to the image server 5 by a data bus, or may be a disk apparatus connected to a storage area network (SAN) or a network attached storage (NAS) connected to the network 10. In a case where the image server 5 receives a request to register a medical image from the imaging apparatus 2, the image server 5 prepares the medical image in a format for a database and registers the medical image in the image DB 6.

Image data of the medical image acquired by the imaging apparatus 2 and accessory information are registered in the image DB 6. The accessory information includes, for example, an image identification (ID) for identifying each medical image, a patient ID for identifying a subject, an examination ID for identifying an examination, a unique ID (unique identification (UID)) allocated for each medical image, examination date and examination time at which a medical image is generated, the type of imaging apparatus used in an examination for acquiring a medical image, patient information such as the name, age, and gender of a patient, an examination part (an imaging part), imaging information (an imaging protocol, an imaging sequence, an imaging method, imaging conditions, the use of a contrast medium, and the like), and information such as a series number or a collection number in a case where a plurality of medical images are acquired in one examination. In the present embodiment, it is assumed that the image DB 6 stores and manages a plurality of medical images of the same patient imaged at different imaging dates and times, or a plurality of medical images of the same patient imaged with different imaging apparatuses. For example, the image DB 6 stores and manages CT images and MRI images acquired at the same time by the CT apparatus and the MRI apparatus for the same patient.

In addition, in a case where the viewing request from the interpretation WS 3 and the medical care WS 4 is received through the network 10, the image server 5 searches for a medical image registered in the image DB 6 and transmits the searched for medical image to the interpretation WS 3 and to the medical care WS 4 that are request sources. In the present embodiment, the image server 5 saves a large amount of supervised training data for training a derivation model 23A, which will be described later. In a case where the image server 5 receives an acquisition request of the supervised training data via the network 10, the image server 5 transmits the supervised training data to the interpretation WS 3 that is the request source.

The report server 7 incorporates a software program for providing a function of a database management system to a general-purpose computer. In a case where the report server 7 receives a request to register the interpretation report from the interpretation WS 3, the report server 7 prepares the interpretation report in a format for a database and registers the interpretation report in the report DB 8.

In the report DB 8, an interpretation report including at least the comments on findings created by the radiologist using the interpretation WS 3 is registered. The interpretation report may include, for example, information such as a medical image to be interpreted, an image ID for identifying the medical image, a radiologist ID for identifying the radiologist who performed the interpretation, a lesion name, lesion position information, information for accessing a medical image including a specific region, and property information.

Further, in a case where the report server 7 receives the viewing request for the interpretation report from the interpretation WS 3 and the medical care WS 4 through the network 10, the report server 7 searches for the interpretation report registered in the report DB 8, and transmits the searched for interpretation report to the interpretation WS 3 and to the medical care WS 4 that are request sources.

In the present embodiment, three-dimensional images such as CT images and MRI images are targeted for interpretation. However, the target of interpretation is not limited to the CT images and the MRI images, and any medical image such as a simple two-dimensional image acquired by a simple X-ray imaging apparatus can be used.

The network 10 is a wired or wireless local area network that connects various apparatuses in a hospital to each other. In a case where the interpretation WS 3 is installed in another hospital or clinic, the network 10 may be configured to connect local area networks of respective hospitals through the Internet or a dedicated line.

Figure 2:
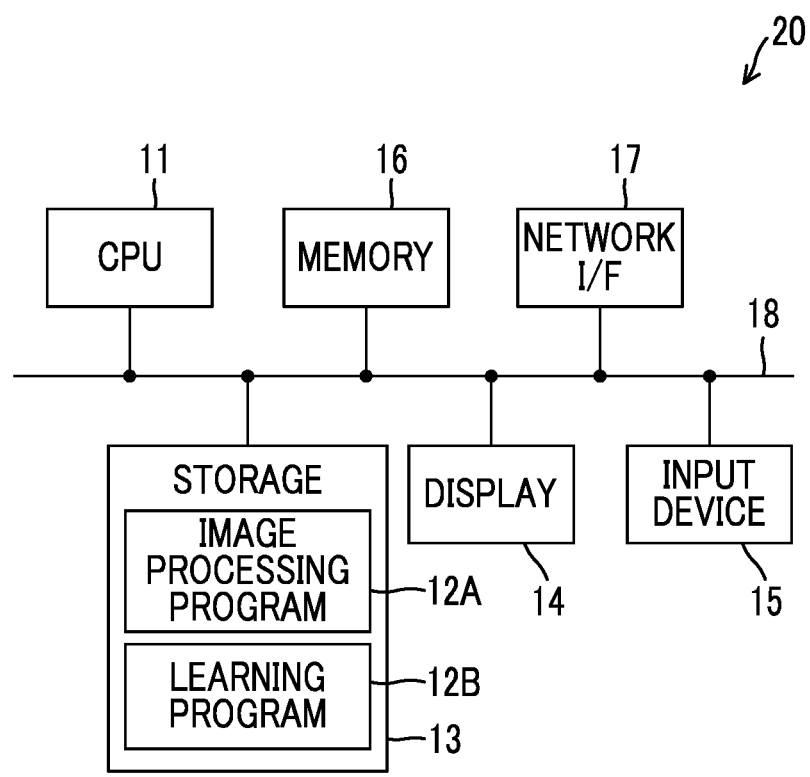
FIG. 2 is a diagram showing a schematic configuration of the image processing apparatus according to the present embodiment.

Next, the image processing apparatus and the learning apparatus according to the embodiment of the present disclosure will be described. FIG. 2 illustrates the hardware configuration of the image processing apparatus and the learning apparatus according to the present embodiment. As shown in FIG. 2, the image processing apparatus and the learning apparatus (hereinafter, represented by the image processing apparatus) 20 includes a central processing unit (CPU) 11, a non-volatile storage 13, and a memory 16 as a temporary storage area. Further, the image processing apparatus 20 includes a display 14 such as a liquid crystal display, an input device 15 such as a keyboard and a mouse, and a network interface (I/F) 17 connected to the network 10. The CPU 11, the storage 13, the display 14, the input device 15, the memory 16, and the network I/F 17 are connected to a bus 18. The CPU 11 is an example of a processor in the present disclosure.

The storage 13 is realized by a hard disk drive (HDD), a solid state drive (SSD), a flash memory, and the like. An image processing program 12A and a learning program 12B are stored in the storage 13 as a storage medium. The CPU 11 reads out the image processing program 12A and the learning program 12B from the storage 13, loads the read-out programs into the memory 16, and executes the loaded image processing program 12A and learning program 12B.

Figure 3:
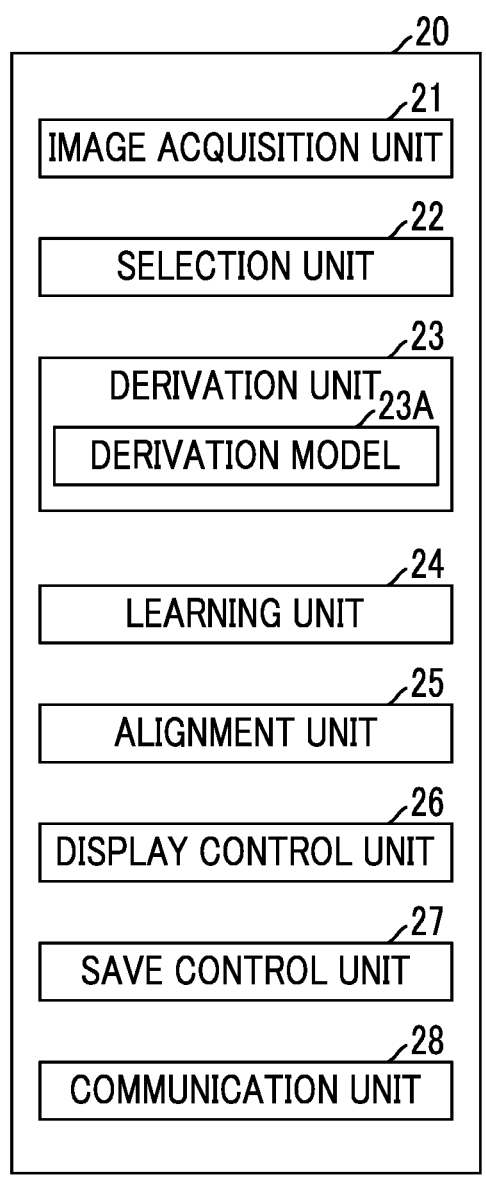
FIG. 3 is a functional configuration diagram of the image processing apparatus according to the present embodiment.

Next, a functional configuration of the image processing apparatus according to the present embodiment will be described. FIG. 3 is a diagram showing a functional configuration of the image processing apparatus according to the present embodiment. As shown in FIG. 3, in the image processing apparatus 20, in a case where the CPU 11 executes the image processing program 12A and the learning program 12B, the CPU 11 functions as an image acquisition unit 21, a selection unit 22, a derivation unit 23, a learning unit 24, an alignment unit 25, a display control unit 26, a save control unit 27, and a communication unit 28.

The image acquisition unit 21 acquires a CT image G1 and an MRI image G2 for creating an interpretation report from the image server 5 according to an instruction from the input device 15 by the radiologist who is an operator. The CT image G1 and the MRI image G2 are acquired by imaging the same patient at the same time. The CT image G1 and the MRI image G2 are three-dimensional images including a plurality of tomographic images. Therefore, in the present embodiment, in a case where the CT image G1 and the MRI image G2 are not distinguished from each other, they may be simply referred to as a three-dimensional image. The CT image G1 and the MRI image G2 are examples of a first three-dimensional image and a second three-dimensional image of the present disclosure.

Figure 4:
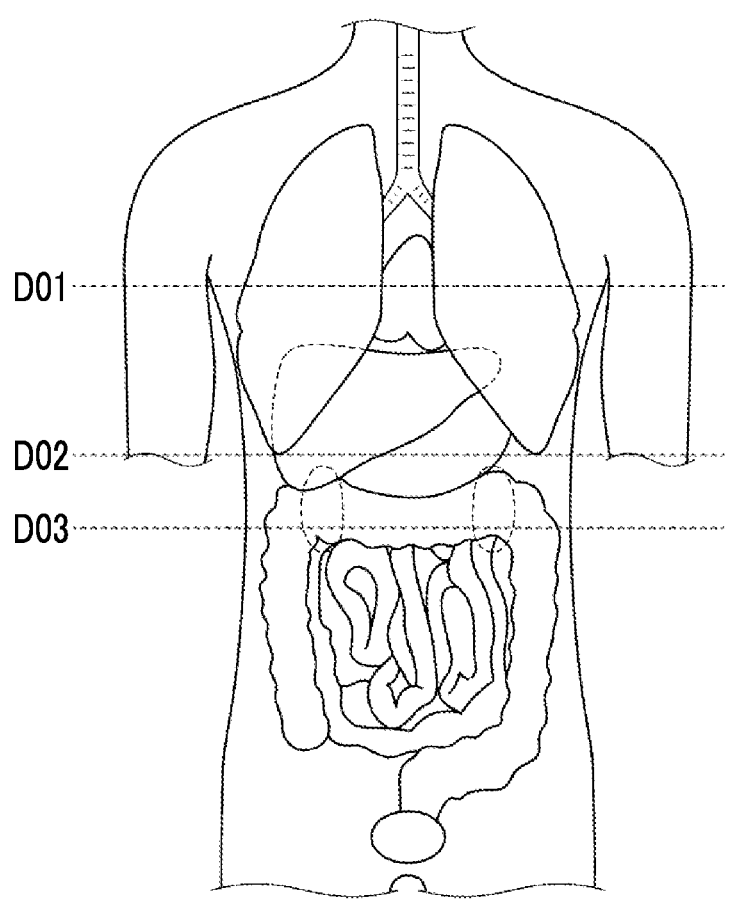
FIG. 4 is a diagram schematically showing a coronal cross section of a body portion of a human body.

The selection unit 22 selects a tomographic image from the CT image G1 and the MRI image G2. Here, the CT image G1 and the MRI image G2 are three-dimensional images, and consist of a plurality of tomographic images representing axial cross sections intersecting the body axis of the patient. FIG. 4 is a diagram schematically showing a coronal cross section of a body portion of the human body. The coronal cross section is a cross section of the patient viewed from the front. In addition to the lungs, heart, liver, stomach, small intestine, large intestine and kidneys (shown by broken lines) shown in FIG. 4, structures such as the brain, bones, and blood vessels exist in the human body, and the structures included in the tomographic image differ depending on the position of the axial cross section. For example, a tomographic image of a tomographic plane D01 includes the lung, the heart, and the like, a tomographic image of a tomographic plane D02 includes the liver, the stomach, and the like, and a tomographic image of a tomographic plane D03 includes the kidney, the large intestine, the small intestine, and the like.

Figure 5:
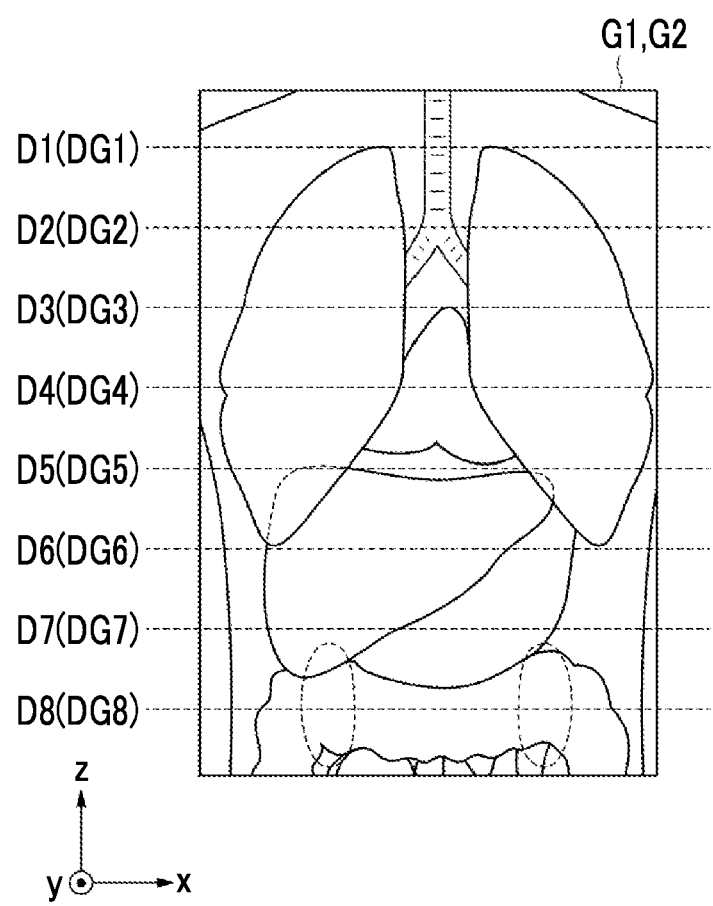
FIG. 5 is a diagram for describing the selection of tomographic images.

In the present embodiment, the selection unit 22 selects a plurality of tomographic images from each of the CT image G1 and the MRI image G2 acquired by the image acquisition unit 21 at predetermined intervals as described above. FIG. 5 is a diagram for describing the selection of tomographic images. As shown in FIG. 5, the selection unit 22 selects a tomographic image DGk (here, k=1 to 8) representing each of a plurality of tomographic planes Dk by thinning out the tomographic images constituting the CT image G1 and the MRI image G2 at equal intervals. In the following description, as shown in FIG. 5, the left-right direction in the case where the human body is viewed from the front is an x direction, the depth direction is a y direction, and the vertical direction, that is, the body axis direction is a z direction. The tomographic plane represented by the tomographic image is the tomographic plane in an xy direction in the three-dimensional image.

Figure 6:
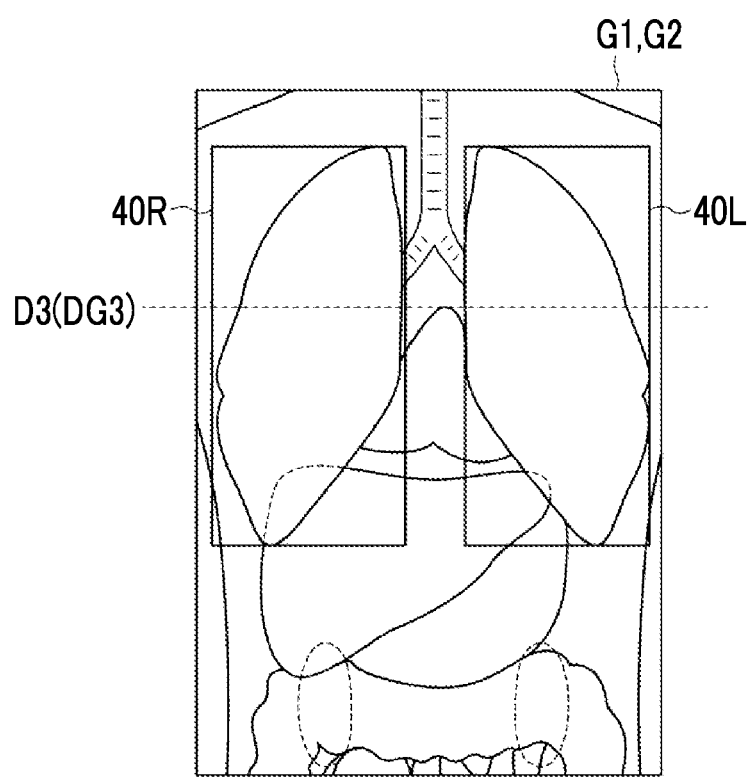
FIG. 6 is a diagram for describing the derivation of three-dimensional coordinate information.

The derivation unit 23 derives three-dimensional coordinate information that defines a position of a structure included in the tomographic image DGk in the tomographic plane from the tomographic image DGk selected by the selection unit 22 in the three-dimensional images G1 and G2, and that defines a position of an end part of the structure outside the tomographic plane in a direction intersecting the tomographic image DGk. For example, with respect to a tomographic image DG3 representing a tomographic plane D3 shown in FIG. 5, the derivation unit 23 derives three-dimensional coordinate information that defines a position of each of the right and left lungs included in the selected tomographic image DG3 in the tomographic plane in the three-dimensional images G1 and G2, and that defines upper and lower end parts of the right and left lungs outside the tomographic plane in a direction intersecting the tomographic image DG3. In the present embodiment, the direction intersecting the tomographic image DG3 is the z direction, which is the body axis direction. As shown in FIG. 6, the three-dimensional coordinate information is coordinate values of a plurality of vertices defining bounding boxes 40R and 40L surrounding the right and left lungs included in the tomographic image DG3 in the three-dimensional images G1 and G2. In FIG. 6 and the following description, it is assumed that the three-dimensional images G1 and G2 are represented by two dimensions and the bounding box is represented by a rectangular region.

Figure 7:
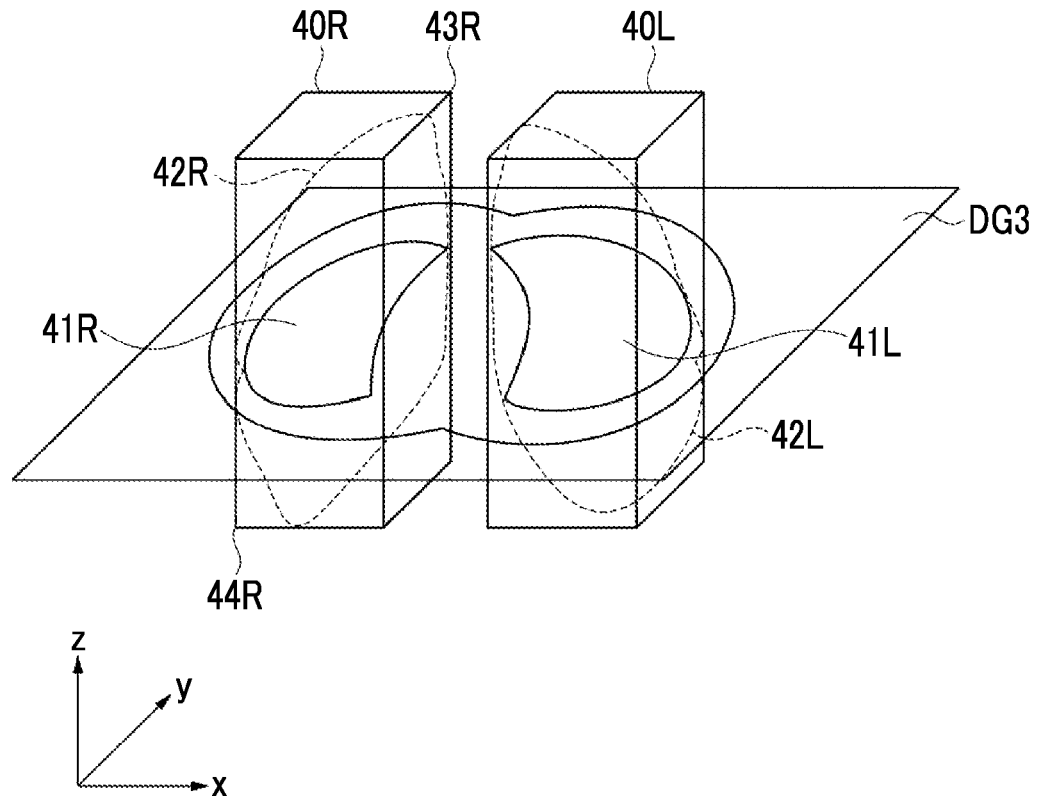
FIG. 7 is a three-dimensional view of a bounding box.

FIG. 7 is a three-dimensional view of the bounding box. As shown in FIG. 7, the tomographic image DG3 includes tomographic images 41R and 41L of the right and left lungs. In the three-dimensional images G1 and G2, the right and left lungs exist as shown by broken lines 42R and 42L in FIG. 7. The derivation unit 23 derives three-dimensional coordinates of a plurality of vertices defining the bounding boxes 40R and 40L surrounding the lung by circumscribing the lung in the three-dimensional image from the tomographic image DG3 as three-dimensional coordinate information.

Here, the bounding boxes 40R and 40L are rectangular cuboids having sides parallel to the x direction, the y direction, and the z direction. In a case where the two vertices at the farthest positions among the eight vertices defining the bounding boxes 40R and 40L are defined, the shape of the rectangular cuboid can be defined. For example, in a case where vertices 43R and 44R shown in FIG. 7 are defined, the shape of the rectangular cuboid of the bounding box 40R can be defined. In the present embodiment, it is assumed that the derivation unit 23 derives the three-dimensional coordinates of the two vertices at the farthest positions among the eight vertices defining the bounding boxes 40R and 40L surrounding the lung, which is a structure in the three-dimensional image, as three-dimensional coordinate information.

In the present embodiment, in order to derive the three-dimensional coordinate information, the derivation unit 23 includes a derivation model 23A that is constructed by performing machine learning using supervised training data to output three-dimensional coordinate information that, in a case where a tomographic image is input, defines a position of a structure included in the input tomographic image in a tomographic plane, and that defines a position of an end part of the structure outside the tomographic plane in a direction intersecting the tomographic image.

Hereinafter, machine learning for constructing the derivation model 23A will be described. Machine learning for constructing the derivation model 23A is performed by the learning unit 24. In the present embodiment, the learning unit 24 the supervised training data constructs the derivation model 23A by machine learning a neural network using supervised training data including a supervised training tomographic image included in a supervised training three-dimensional image and supervised training three-dimensional coordinate information that defines a position of the structure included in the supervised training three-dimensional image in the tomographic plane, and that defines the position of the end part of the structure outside the tomographic plane in a direction intersecting the supervised training tomographic image.

Here, as a neural network, regions with CNN features (Faster-RCNN) using a convolutional neural network (hereinafter referred to as CNN), which is one of the multi-layer neural networks in which deep learning is performed, is known (see, for example, U.S. Pat. No. 9,858,496B and "Ren, Shaoqing, et al. "Faster R-CNN: Towards real-time object detection with region proposal networks." Advances in neural information processing systems. 2015"). In the present embodiment, it is assumed that the derivation model 23A is constructed by machine learning a network based on Faster-RCNN.

Note that the network for constructing the derivation model 23A is not limited to the one based on Faster-RCNN. For example, the derivation model 23A may be constructed based on other object detection models such as "Wei Liu et al., "SSD: Single Shot MultiBox Detector", ECCV, 2016", "Joseph Redmon et al., "You Only Look Once: Unified, Real-Time Object Detection", arXiv, 2016", "Mingxing Tan et al., "EfficientDet: Scalable and Efficient Object Detection", arXiv, 2020", or "Nicolas Carion et al., "End-to-End Object Detection with Transformers", arXiv, 2020".

Figure 8:
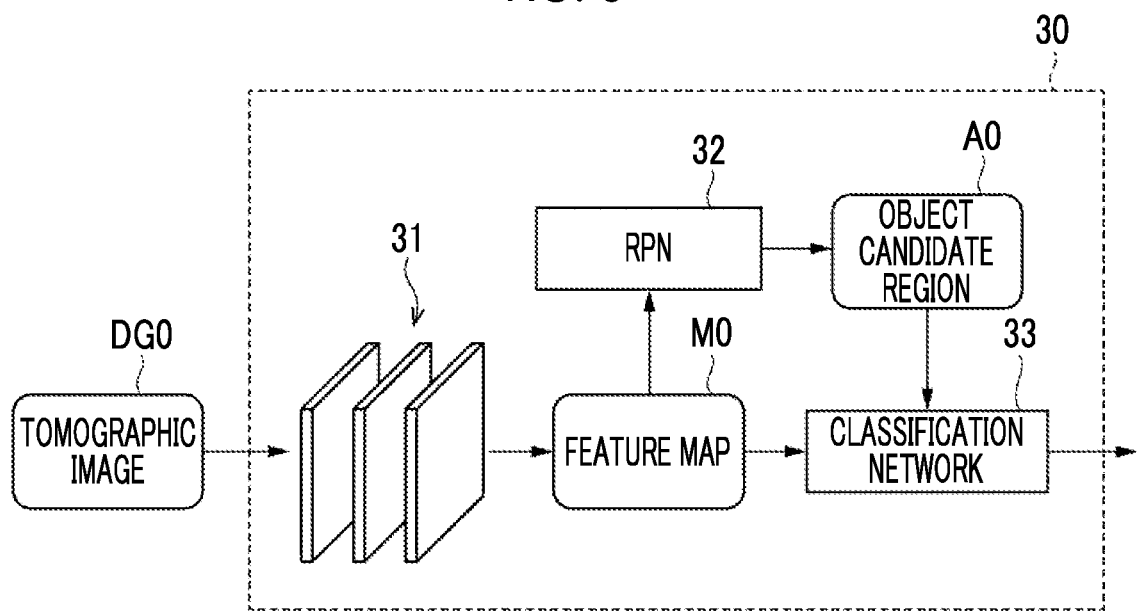
FIG. 8 is a block diagram showing a configuration of a network used in a derivation model in the present embodiment.

Here, Faster-RCNN includes a convolutional layer that extracts a feature amount from an input image to generate a feature map, region proposal networks (RPNs) that specify a candidate region of an object in the input image, and a classification network that uses the feature map and the object candidate region as inputs and outputs the results of classification and regression of object categories. FIG. 8 is a block diagram showing a configuration of a network based on the Faster-RCNN used in the derivation model 23A in the present embodiment. As shown in FIG. 8, a network 30 includes a convolutional layer 31 that generates a feature map MO from a tomographic image DG0 that is an input image, an RPN 32 that specifies a candidate region of a structure included in the feature map MO, and a classification network 33 that classifies the candidate regions based on the feature map MO and the candidate regions of the structure and outputs the three-dimensional coordinate information of the classified structures.

The convolutional layer 31 performs convolution processing using various kernels on the input tomographic image DG0, and outputs a feature map consisting of feature data obtained by the convolution processing. The kernel has an n×n pixel size (for example, n=3), and weights are set for each element. Specifically, weights such as a differential filter that emphasizes edges of the input image are set. The convolutional layer 31 applies the kernel to the entire input image or the feature map output from the processing layer in the previous stage while shifting attention pixels of the kernel. Furthermore, the convolutional layer 31 applies an activation function such as a sigmoid function to the convolved value, and outputs the feature map MO.

In the RPN 32, a rectangular region called an anchor having a plurality of types of aspect ratios and sizes is defined in advance. In the RPN 32, a plurality of types of anchors are applied to each pixel position of the feature map MO generated from the tomographic image DG0, and the anchor having the largest overlap rate with the object candidate included in the tomographic image DG0 is selected. Then, in the RPN 32, using the selected anchor, a process of regressing (that is, deforming and moving) the anchor so as to match a rectangle (correct answer box) surrounding the object candidate is performed on all the pixels of the feature map MO, and the position and size of the anchor regressed so as to match the correct answer box are output from the RPN 32 as an object candidate region AO in the input tomographic image DG0.

The classification network 33 consists of fully connected layers, and classifies the object candidate regions in the tomographic image DG0 and derives the three-dimensional coordinate information of the classified structures based on the object candidate region AO and the feature map MO. Specifically, for each pixel of the tomographic image DG0, a score indicating that the object candidate region AO is a specific region is derived, and the pixel is classified into a structure having the maximum score. The score takes a value of 0 to 1. The classification network also outputs three-dimensional coordinate information defining a bounding box surrounding a region consisting of classified pixels.

Figure 9:
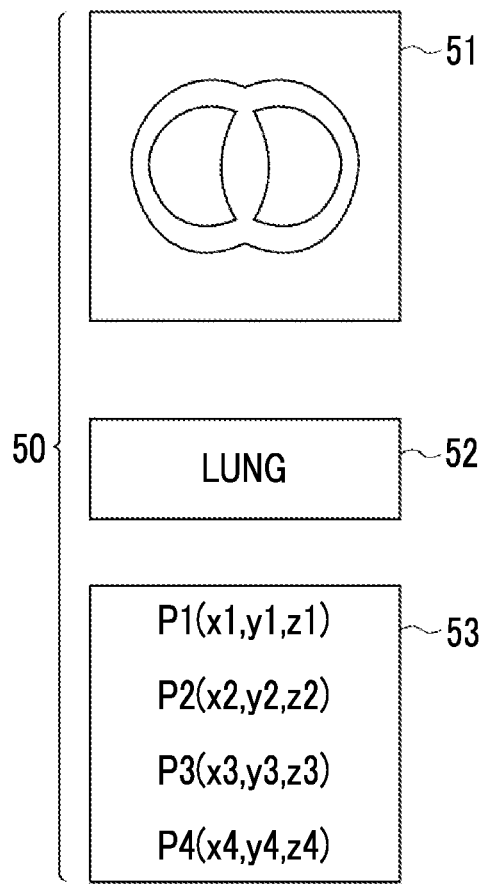
FIG. 9 is a diagram showing an example of supervised training data.

Next, the supervised training data for machine learning the network 30 in the derivation model 23A will be described. FIG. 9 is a diagram showing an example of supervised training data. As shown in FIG. 9, supervised training data 50 includes a supervised training tomographic image 51 included in the supervised training three-dimensional image, a label 52 representing a structure included in the supervised training tomographic image 51, and supervised training three-dimensional coordinate information 53 that defines a position of the structure included in the supervised training tomographic image 51 in the tomographic plane in the supervised training three-dimensional image, and that defines the position of the end part of the structure outside the tomographic plane in a direction intersecting the tomographic image. The number of supervised training tomographic images 51 included in the supervised training data 50 is not limited to one, and may be plural.

Figure 10:
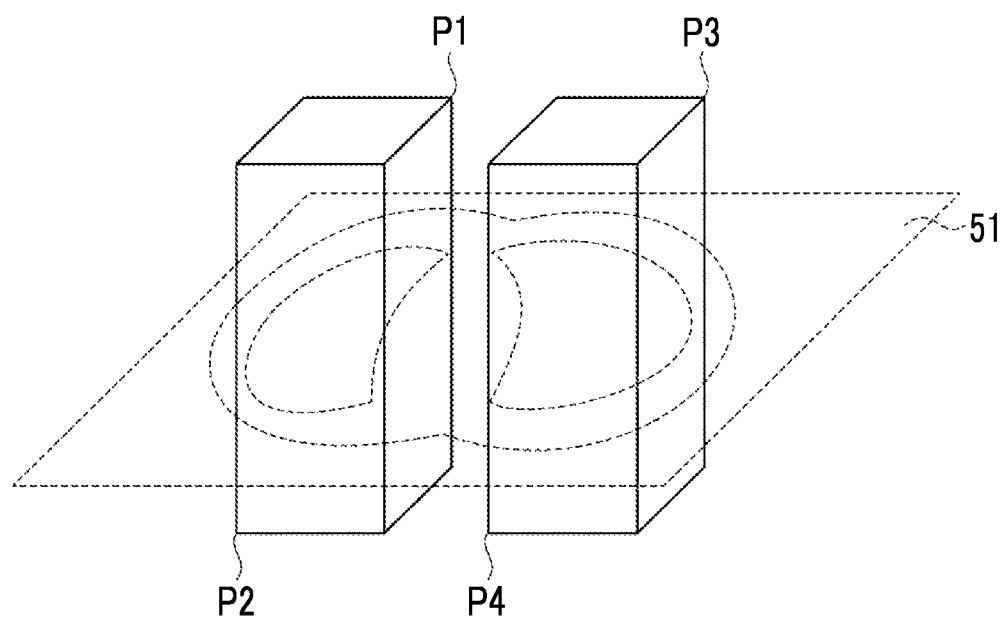
FIG. 10 is a diagram for describing a relationship between a bounding box and three-dimensional coordinate information.

As shown in FIG. 9, the supervised training tomographic image 51 includes the right and left lungs as a structure. The content of the label 52 is "lung". The supervised training three-dimensional coordinate information 53 includes three-dimensional coordinates P1 (x1, y1, z1) and P2 (x2, y2, z2) defining the bounding box surrounding the right lung included in the supervised training three-dimensional image, and three-dimensional coordinates P3 (x3, y3, z3) and P4 (x4, y4, z4) surrounding the left lung. As shown in FIG. 10, the three-dimensional coordinates P1 and P2 define the positions of the two most distant points of the bounding box surrounding the right lung included in the supervised training tomographic image 51 in the supervised training three-dimensional image. The three-dimensional coordinates P3 and P4 define the positions of the two most distant points of the bounding box surrounding the left lung included in the supervised training tomographic image 51 in the supervised training three-dimensional image. Here, the z-coordinates of the three-dimensional coordinates P1 to P4 defining the bounding box may have a value based on the supervised training three-dimensional image, but in the present embodiment, it is assumed that the z-coordinates have a value based on the supervised training tomographic image 51. For example, in the present embodiment, the z-coordinate values of the three-dimensional coordinates P1 to P4 of the bounding box are determined by setting the z-coordinate value of each pixel of the supervised training tomographic image 51 to 0.

In the present embodiment, the three-dimensional image is a CT image and an MRI image. Here, the various structures included in the human body have different distribution ranges of brightness values between the CT image and the MRI image even though they are the same structure. Therefore, the supervised training tomographic image 51 included in the supervised training data is processed to match the distribution range of the brightness values regardless of whether it is a CT image or an MRI image. As a process for matching the distribution range of the brightness values, for example, the brightness value of the MRI image may be matched with the brightness value of the CT image, and the brightness value of the CT image may be matched with the brightness value of the MRI image. The process of matching the distribution range of the brightness values may be performed by using, for example, a conversion table or a conversion formula for converting the brightness values. Further, in each of the CT image and the MRI image, the distribution range of the brightness values may be matched by performing the normalization process so that the brightness value distribution in the image falls within the range of 0 to 1. Normalization may be performed by obtaining a standard deviation of the brightness value distribution in the image for each of the CT image and the MRI image to divide the brightness value of each voxel in the image by the standard deviation or a constant multiple of the standard deviation, or the like.

The learning unit 24 inputs the supervised training tomographic image 51 included in the supervised training data 50 into the network 30, and outputs a score representing the classification result of the structure included in the supervised training tomographic image 51 and three-dimensional coordinate information defining the end part of the structure. In this case, the score is derived in the range of 0 to 1 for each of the plurality of types of structures that can be included in the supervised training tomographic image 51. The learning unit 24 derives an error between the derived score and 1 as a loss so that the score of the structure defined on the label 52 becomes 1. Then, based on the derived loss, the convolutional layer 31, the RPN 32, and the classification network 33 constituting the network 30 are trained by using the stochastic gradient descent method or the backpropagation method.

Further, the learning unit 24 derives an error between the derived three-dimensional coordinate information and the supervised training three-dimensional coordinate information 53 included in the supervised training data 50 as a loss. Then, the convolutional layer 31, the RPN 32, and the classification network 33 constituting the network 30 are trained by using the stochastic gradient descent method or the backpropagation method so that the loss is minimized. Specifically, the network 30 is trained by deriving the number of layers in the convolutional layer 31 included in the network 30, the number of pooling layers, the coefficient of the kernel, the size of the kernel, and the like, deriving the position and size of the anchor in the RPN 32 and the like, and deriving the weight of the bond in the fully connected layer constituting the classification network 33 and the like.

Thereby, in a case where the tomographic image is input, the network 30 outputs the classification result of the structures included in the tomographic image and the three-dimensional coordinate information of the bounding box surrounding the classified structures in the three-dimensional image.

Figure 11:
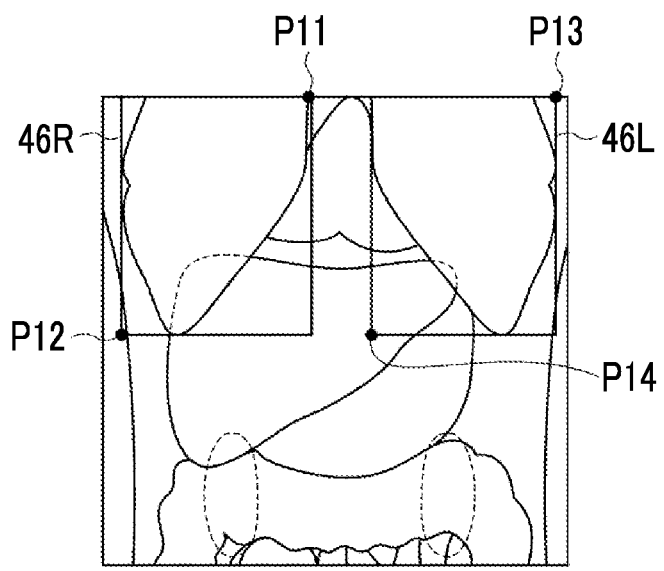
FIG. 11 shows a three-dimensional image in which lungs are cut off.

Note that the structure included in the three-dimensional image may be cut off in the three-dimensional image. For example, in the case of a three-dimensional image acquired by taking a picture centering on the liver as shown in FIG. 11, the upper side of the lung is cut off. In a case of deriving supervised training data about the lungs using such a three-dimensional image as a supervised training three-dimensional image, it is possible to obtain supervised training three-dimensional coordinate information of the bounding box surrounding the lung for the lower side (foot side) of the lungs. However, it is not possible to obtain the supervised training three-dimensional coordinate information of the bounding box for the upper side (head side) of the lung.

In a case where the supervised training data is generated from such a supervised training three-dimensional image in which the lung is cut off, the three-dimensional coordinate information about the bounding box surrounding the lung is used as the supervised training three-dimensional coordinate information within the range included in the supervised training three-dimensional image. Specifically, as shown in FIG. 11, for the right lung, the three-dimensional coordinate information of the two most distant vertices P11 and P12 for a bounding box 46R is used as the supervised training three-dimensional coordinate information. For the left lung, the three-dimensional coordinate information of the two most distant vertices P13 and P14 for a bounding box 46L is used as the supervised training three-dimensional coordinate information. In addition, the supervised training data is flagged to indicate that the upper side of the lung is cut off.

Then, in the case of training the network 30 using such supervised training data, regarding the three-dimensional coordinate information output from the network 30, the learning unit 24 trains the network 30 by reducing the weight for the error with the supervised training data, that is, the loss, for the three-dimensional coordinates on the upper side of the lung. Thereby, in the supervised training three-dimensional image for which supervised training data is generated, even in a case where the structure is cut off in the z direction, the network 30 can be trained by reducing the influence of the cut-off structure.

Figure 12:
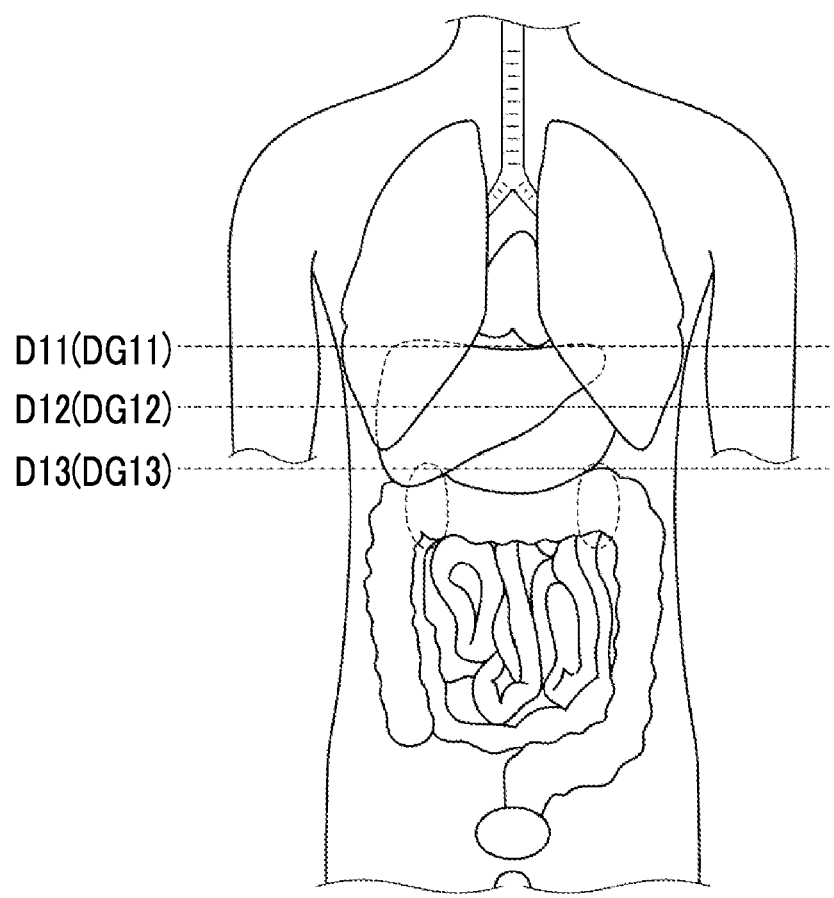
FIG. 12 is a diagram for describing the derivation of supervised training data according to the position of a tomographic plane of a liver.
Figure 13:
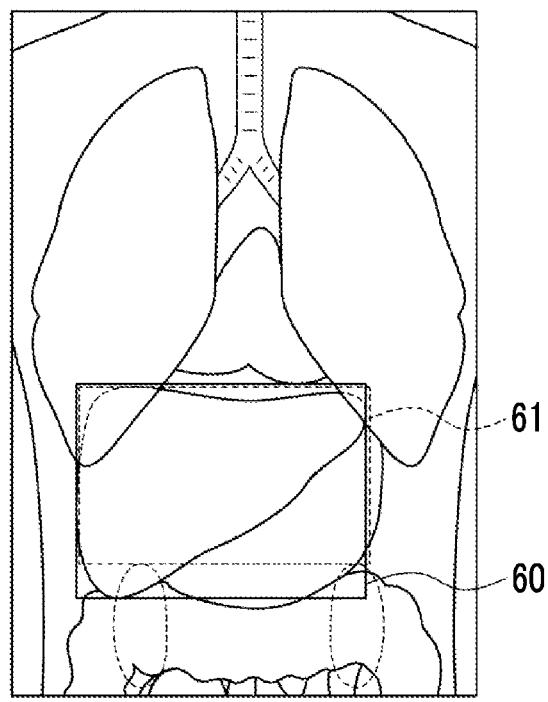
FIG. 13 is a diagram for describing an accuracy of deriving three-dimensional coordinate information.

Further, for the structure included in the tomographic image, the accuracy of deriving the three-dimensional coordinate information using the network 30 differs depending on the position of the tomographic plane of the structure in the z direction. For example, as shown in FIG. 12, a case where supervised training data is derived for each of an upper tomographic plane D11, a middle tomographic plane D12, and a lower tomographic plane D13 of the liver is considered. FIG. 13 is a diagram for describing the accuracy of deriving the three-dimensional coordinate information. In FIG. 13, a bounding box 60 surrounding the liver is shown by a solid line, and a bounding box based on the three-dimensional coordinate information output by the network 30 (hereinafter referred to as an output bounding box) 61 is shown by a broken line. As shown in FIG. 13, in a case where a tomographic image DG11 representing the upper tomographic plane D11 of the liver is input to the network 30, the accuracy of the output three-dimensional coordinate information on the upper side of the liver is high, but the accuracy of the three-dimensional coordinate information on the lower side is low. Therefore, in the upper part of the liver, the output bounding box 61 substantially matches the bounding box 60, but in the lower part of the liver, the output bounding box 61 is significantly different from the bounding box 60. On the contrary, in a case where a tomographic image DG13 representing the lower tomographic plane D13 of the liver is input to the network 30, the accuracy of the output three-dimensional coordinate information on the lower side of the liver is high, but the accuracy of the three-dimensional coordinate information on the upper side is low.

Figure 14:
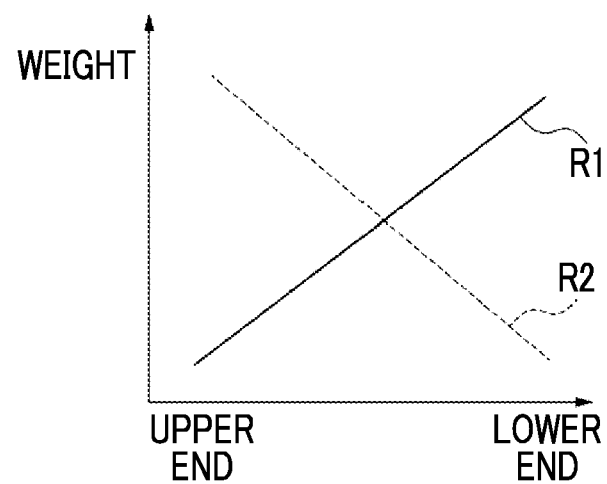
FIG. 14 is a diagram showing a relationship between a relative position of a tomographic image viewed from a certain organ and a weight with respect to a loss.

Therefore, in the case of learning the network 30, the learning unit 24 trains the network 30 by changing the weight of the loss with the supervised training data according to the position of the tomographic plane in the z direction of the structure included in the supervised training tomographic image included in the supervised training data with respect to the z-coordinate of the three-dimensional coordinate information output by the network 30. FIG. 14 is a diagram showing a relationship between a relative position of a tomographic image viewed from a certain organ and a weight with respect to a loss. In FIG. 14, a solid line R1 represents a weighting coefficient for an error (that is, loss) between "three-dimensional coordinates of the lower end of the structure" predicted from the tomographic image and correct supervised training three-dimensional coordinates. A broken line R2 represents a weighting coefficient for an error between "three-dimensional coordinates of the upper end of the structure" predicted from the tomographic image and correct supervised training three-dimensional coordinates.

Here, the larger the value of the weighting coefficient, the larger the loss at the time of learning, that is, the penalty for the error from the correct answer.

As shown by the solid line R1, in a case where the tomographic image is near the upper end of the organ, the weight becomes small because it is difficult to predict the three-dimensional coordinates of the lower end. On the contrary, in a case where the tomographic image is near the lower end of the organ, the weight becomes large because it is easy to predict the three-dimensional coordinates of the lower end. On the other hand, as shown by the broken line R2, in a case where the tomographic image is near the upper end of the organ, the weight becomes large because it is easy to predict the three-dimensional coordinates of the upper end. On the contrary, in a case where the tomographic image is near the lower end of the organ, the weight becomes small because it is difficult to predict the three-dimensional coordinates of the upper end.

In a case where the tomographic image DG11 representing the upper tomographic plane D11 of the liver shown in FIG. 12 described above is used as the supervised training tomographic image by using the weight as shown in FIG. 14, regarding the three-dimensional coordinate information output from the network 30 in the derivation model 23A, the weight for loss becomes large for the three-dimensional coordinate information on the upper end side, and the weight for loss becomes small for the three-dimensional coordinate information on the lower end side. Further, a case where the tomographic image DG13 representing the lower tomographic plane D13 of the liver shown in FIG. 12 described above is used as the supervised training tomographic image, regarding the three-dimensional coordinate information output from the network 30, the weight for loss becomes large for the three-dimensional coordinate information on the lower end side, and the weight for loss becomes small for the three-dimensional coordinate information on the upper end side.

Thereby, even in a case where the supervised training data including the supervised training tomographic image whose accuracy for deriving the three-dimensional coordinate information is not so good is used, the influence of such supervised training data on the learning of the network 30 can be reduced. Therefore, the network 30 can be trained so that the three-dimensional coordinate information defining the upper end and the lower end of the structure can be derived more accurately.

The derivation model 23A is constructed by machine learning as described above.

Therefore, in a case where the tomographic image is input, the derivation model 23A outputs the three-dimensional coordinate information defining the bounding box surrounding the structure included in the input tomographic image. For example, in a case where the selection unit 22 selects a tomographic image DG5 representing a tomographic plane D5 shown in FIG. 5, the derivation unit 23 derives the three-dimensional coordinate information in the three-dimensional images G1 and G2 about the left lung, the right lung, and the liver included in the tomographic image DG5. The three-dimensional coordinate information derived for the CT image G1 corresponds to first three-dimensional coordinate information of the present disclosure, and the three-dimensional coordinate information derived for the MRI image G2 corresponds to second three-dimensional coordinate information of the present disclosure.

Here, the z-coordinate included in the three-dimensional coordinate information defining the bounding box output by the derivation model 23A is based on the tomographic image input to the derivation model 23A. That is, the z-coordinate included in the three-dimensional coordinate information defining the bounding box output by the derivation model 23A has a value when the z-coordinate value of the tomographic image is set to 0. Therefore, in order to match the z-coordinate included in the three-dimensional coordinate information defining the bounding box with the coordinate system of the three-dimensional images G1 and G2, the derivation unit 23 corrects the z-coordinate included in the three-dimensional coordinate information output by the derivation model 23A based on the z-coordinate in the three-dimensional images G1 and G2 of the tomographic image input to the derivation model 23A. The correction may be performed by adding the z-coordinate values in the three-dimensional images G1 and G2 of the tomographic image to the z-coordinate included in the three-dimensional coordinate information defining the bounding box output by the derivation model 23A.

Figure 15:
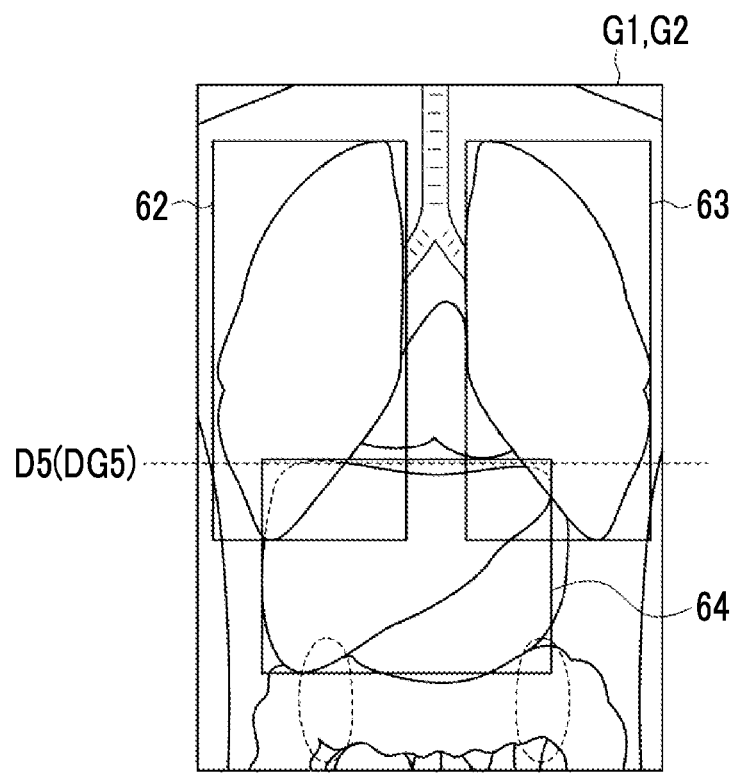
FIG. 15 is a diagram for describing the derivation of three-dimensional coordinate information.

By using the three-dimensional coordinate information derived in this way, as shown in FIG. 15, a bounding box 62 surrounding the right lung, a bounding box 63 surrounding the left lung, and a bounding box 64 surrounding the liver can be set in the three-dimensional images G1 and G2.

Here, in the case of deriving the three-dimensional coordinate information, the derivation unit 23 performs preprocessing for matching the distribution ranges of the brightness values of the CT image G1 and the MRI image G2. The preprocessing may be performed in the same manner as in the case of generating the supervised training tomographic image of the supervised training data described above.

Figure 16:
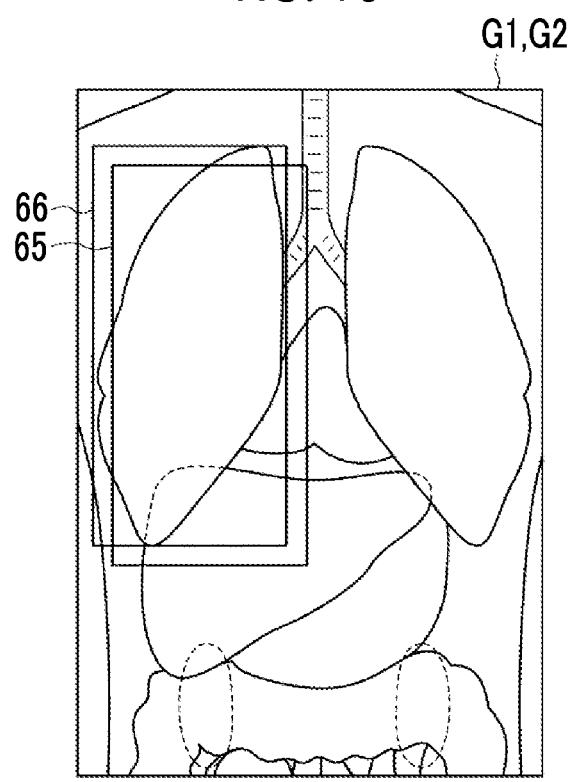
FIG. 16 is a diagram for describing the derivation of three-dimensional coordinate information.

The derivation unit 23 derives three-dimensional coordinate information defining the upper end and the lower end of the structure included in the tomographic images DG1 to DG8 for each of the plurality of tomographic images DG1 to DG8 selected as shown in FIG. 5. In this case, the derivation unit 23 derives, for example, three-dimensional coordinate information defining a bounding box surrounding the lung in the three-dimensional image for each of the plurality of tomographic images DG2 to DG6 including the lung. However, the three-dimensional coordinate information output by the derivation model 23A does not always match in all tomographic images even though the structures are the same. For example, for the right lung, a bounding box defined by three-dimensional coordinate information derived from the tomographic image DG2 (hereinafter referred to as a bounding box based on the tomographic image DG2) and a bounding box defined by three-dimensional coordinate information derived from the tomographic image DG5 (hereinafter referred to as a bounding box based on the tomographic image DG5) are considered. As shown in FIG. 16, the positions of a bounding box 65 based on the tomographic image DG2 and a bounding box 66 based on the tomographic image DG5 do not completely match.

Therefore, the derivation unit 23 outputs a plurality of pieces of provisional three-dimensional coordinate information for each of the plurality of tomographic images including the common structure by the derivation model 23A. Then, the derivation unit 23 integrates the plurality of pieces of provisional three-dimensional coordinate information output by the derivation model 23A to derive the three-dimensional coordinate information about the common structure. Specifically, the derivation unit 23 derives the average value of the provisional three-dimensional coordinate information output by the derivation model 23A for each of the plurality of tomographic images, and uses the derived average value as three-dimensional coordinate information about the common structure included in the plurality of tomographic images. In this case, the average value may be an arithmetic mean value.

Figure 17:
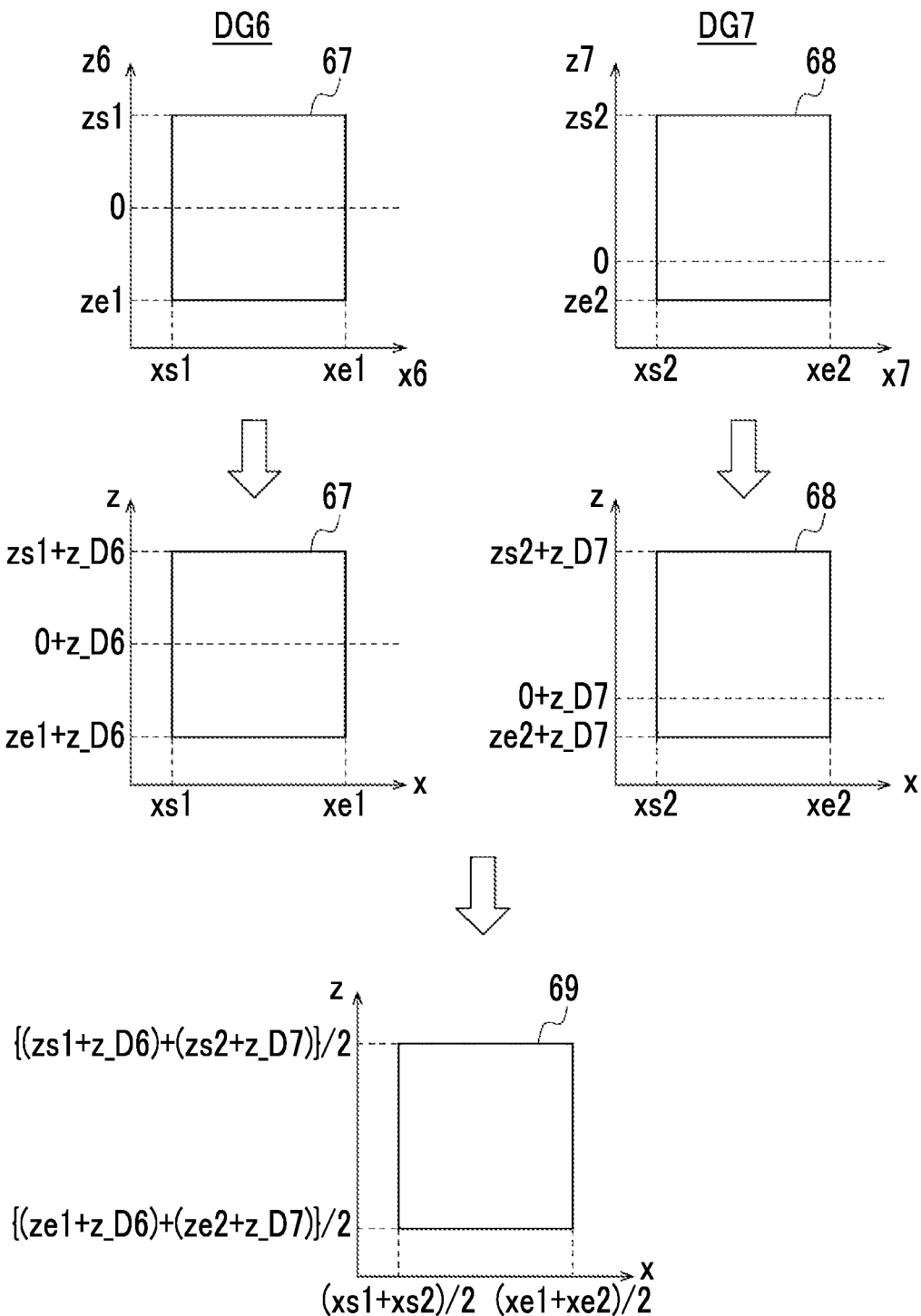
FIG. 17 is a diagram for describing the integration of provisional three-dimensional coordinate information.

The coordinates included in the provisional three-dimensional coordinate information are based on each of the tomographic images from which the provisional three-dimensional coordinate information is derived. Therefore, at the time of integration, it is necessary to convert the coordinate system of a plurality of pieces of provisional three-dimensional coordinate information into a common coordinate system, for example, the coordinate system of the three-dimensional images G1 and G2, and then calculate the average value and the like of the plurality of pieces of provisional three-dimensional coordinate information. Hereinafter, the integration will be described in detail. FIG. 17 is a diagram for describing the integration of provisional three-dimensional coordinate information. In the following description, it is assumed that the three-dimensional coordinate information of the bounding box surrounding the liver is obtained by using the two tomographic images DG6 and DG7 shown in FIG. 5. Further, in FIG. 17, for the sake of description, an integration process using a tomographic image of an axial cross section is shown.

As shown in FIG. 17, it is assumed that a bounding box 67 is derived based on the tomographic image DG6 and a bounding box 68 is derived based on the tomographic image DG7. It is assumed that the coordinate system of the bounding box 67 is an x6-z6 coordinate system based on the tomographic image DG6. It is assumed that the coordinate system of the bounding box 68 is an x7-z7 coordinate system based on the tomographic image DG7. The upper and lower z-coordinates based on the provisional three-dimensional coordinate information of the bounding box 67 are set to zs1 and ze1, respectively, and the left and right x-coordinates are set to xs1 and xe1, respectively. In the x6-z6 coordinate system, the z-coordinate value of the position of the tomographic image DG6 is 0. Further, the upper and lower z-coordinates based on the provisional three-dimensional coordinate information of the bounding box 68 are set to zs2 and ze2, respectively, and the left and right x-coordinates are set to xs2 and xe2, respectively. In the x7-z7 coordinate system, the z-coordinate value of the position of the tomographic image DG7 is 0.

The derivation unit 23 converts the coordinate systems of the bounding boxes 67 and 68 into the coordinate systems of the three-dimensional images G1 and G2 at the time of integration. Here, in the coordinate systems of the three-dimensional images G1 and G2, assuming that the z-coordinate of the tomographic image DG6 is z_D6 and the z-coordinate of the tomographic image DG7 is z_D7, the derivation unit 23 converts the coordinate system by adding z_D6 to the upper and lower z-coordinates of the bounding box 67, and adding z_D7 to the upper and lower z-coordinates of the bounding box 68. Thereby, the upper and lower z-coordinates of the bounding box 67 are zs1+z_D6 and ze1+z_D6, respectively. Further, the upper and lower z-coordinates of the bounding box 68 are zs2+z_D7 and ze2+z_D7, respectively. Note that the x-coordinate and y-coordinate of the bounding boxes 67 and 68 are not converted.

Then, the derivation unit 23 integrates the provisional three-dimensional coordinate information by calculating the average value of the provisional three-dimensional coordinate information after the coordinate conversion for each of the bounding boxes 67 and 68. Specifically, the provisional three-dimensional coordinate information is integrated by calculating the arithmetic mean of the z-coordinate and the x-coordinate of the bounding boxes 67 and 68 after the coordinate conversion. Thereby, the upper z-coordinate of the integrated bounding box 69 is {(zs1+z_D6)+(zs2+z_D7)}/2, and the lower z-coordinate thereof is {(ze1+z_D6)+(ze2+z_D7)}/2. The left x-coordinate of the bounding box 69 is (xs1+xs2)/2, and the right x-coordinate thereof is (xe1+xe2)/2. The coordinate values of the bounding box 69 in the y-axis direction may be calculated in the same manner as in the x-axis direction.

On the other hand, as in the case of training the network 30 constituting the derivation model 23A as described above, the accuracy of the three-dimensional coordinate information output by the derivation model 23A differs depending on the position of the tomographic plane in the z direction of the structure included in the tomographic image. For example, in a case where the tomographic image DG2 representing the tomographic plane D2 shown in FIG. 5 is used, the accuracy of the three-dimensional coordinate information on the upper end side of the lung is high, but the accuracy of the three-dimensional coordinate information on the lower end side of the lung is not as high as that of the upper end side. On the other hand, in a case where the tomographic image DG5 representing the tomographic plane D5 is used, the accuracy of the three-dimensional coordinate information on the lower end side of the lung is high, but the accuracy of the three-dimensional coordinate on the upper end side of the lung is not as high as that of the lower end side. Therefore, in the case of integrating the provisional three-dimensional coordinate information of the structures derived for each tomographic image, it is preferable to derive the weighted average value according to the position of the tomographic plane in the z direction of the structure included in each tomographic image as final three-dimensional coordinate information.

For example, for the sake of description, in a case where the three-dimensional coordinate information on the upper end side of the right lung output by the derivation model 23A and converted into a common coordinate system for the four tomographic images DG2 to DG5 each representing the four tomographic planes D2 to D5 is denoted by Pu22 to Pu25, final three-dimensional coordinate information Pu0 on the upper end side of the right lung is derived by the following Equation (1). Further, in a case where the three-dimensional coordinate information on the lower end side of the right lung output by the derivation model 23A and converted into a common coordinate system is denoted by P122 to P125, final three-dimensional coordinate information P10 on the lower end side of the right lung is derived by the following Equation (2).

$$Pu0 = w12*Pu22 + w13*Pu23 + w14*Pu24 + w15*Pu25 \quad (1)$$

$$P10 = w22*P122 + w23*P123 + w24*P124 + w25*P125 \quad (2)$$

In Equation (1), w12 to w15 are weighting coefficients, and w12+w13+w14+w15=1 and w12>w13>w14>w15. In Equation (2), w22 to w25 are weighting coefficients, w22+w23+w24+w25=1 and w22<w23<w24<w25. Thereby, even in a case where a common structure is included in the plurality of tomographic images, the three-dimensional coordinate information can be accurately derived regardless of the position of the tomographic plane in the z direction of the structure.

The alignment unit 25 aligns the CT image G1 and the MRI image G2. To this end, the alignment unit 25 sets bounding boxes for the CT image G1 and the MRI image G2 by using the three-dimensional coordinate information of the structure included in the CT image G1 and the three-dimensional coordinate information of the structure included in the MRI image G2, which are derived by the derivation unit 23. Then, the alignment unit 25 aligns the CT image G1 and the MRI image G2 using the bounding boxes.

Figure 18:
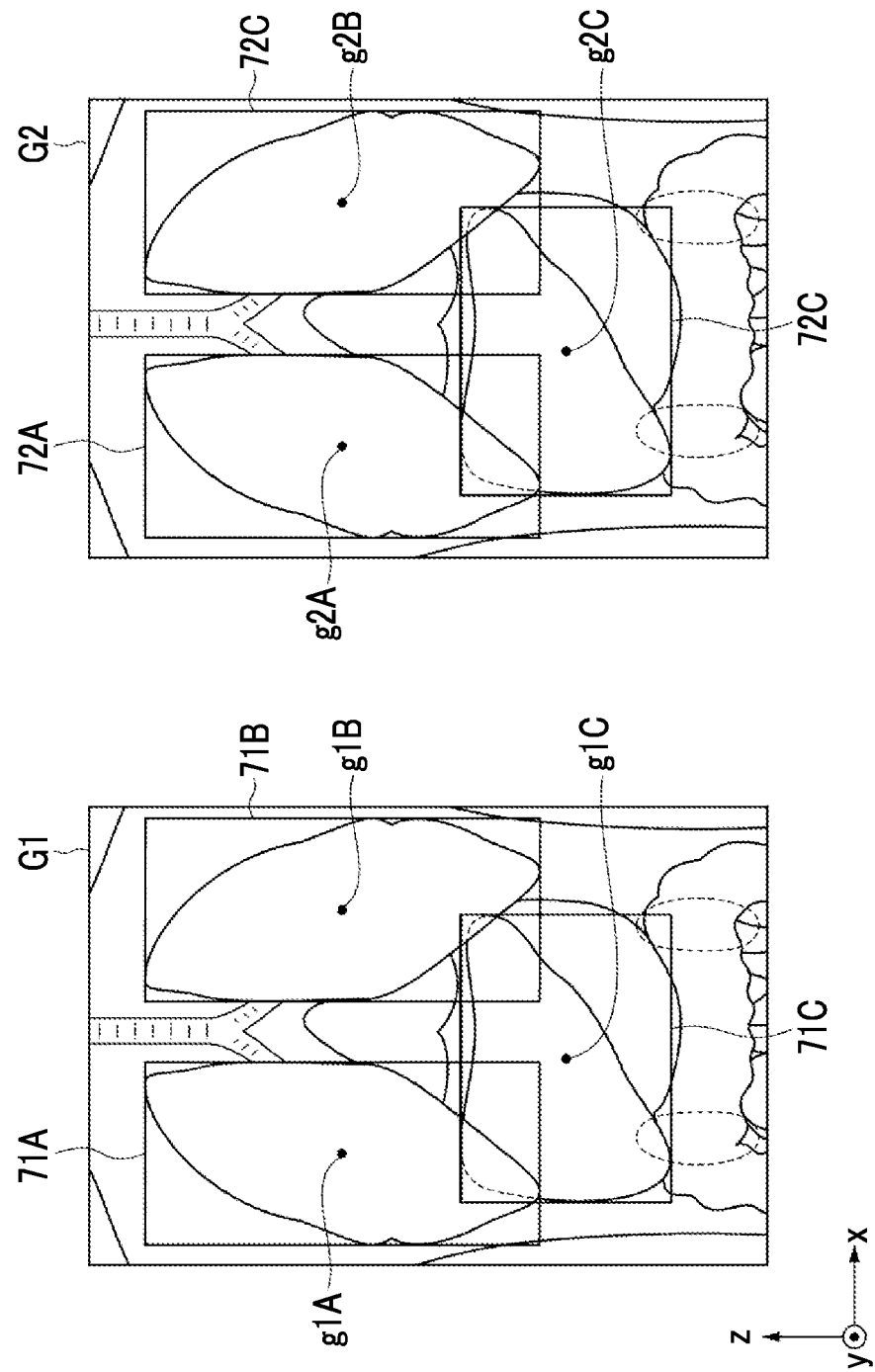
FIG. 18 is a diagram for describing alignment.

FIG. 18 is a diagram for describing the alignment between the CT image and the MRI image. Here, it is assumed that bounding boxes 71A to 71C and 72A to 72C are set only for the right lung, the left lung, and the liver in each of the CT image G1 and the MRI image G2.

The alignment unit 25 derives respective centroid positions g1A to g1C of the bounding boxes 71A to 71C in the CT image G1. Further, the alignment unit 25 derives respective centroid positions g2A to g2C of the bounding boxes 72A to 72C in the MRI image G2. Then, the CT image G1 and the MRI image G2 are aligned so that the positions of the centroid positions g1A to g1C and the centroid positions g2A to g2C corresponding to each other in the x direction, the y direction, and the z direction match. Specifically, the alignment unit 25 derives an alignment amount including at least one of the translation amount, the magnification ratio, or the rotation amount of the MRI image G2 with respect to the CT image G1 by using, for example, the least square method so that a sum of a difference between the centroid position g1A and the centroid position g2A, a difference between the centroid position g1B and the centroid position g2B, and a difference between the centroid position g1C and the centroid position g2C is minimized. Then, the alignment unit 25 aligns the CT image G1 and the MRI image G2 by translating, scaling, and/or rotating one of the CT image G1 and the MRI images G2 with respect to the other of the CT image G1 and the MRI images G2 based on the derived alignment amount.

A first integrated centroid position in which the centroid positions g1A to g1C derived for the CT image G1 are integrated and a second integrated centroid position in which the centroid positions g2A to g2C derived for the MRI image G2 are integrated may be derived, and the alignment may be performed so that the derived first integrated centroid position and second integrated centroid position match. Further, the alignment may be performed using only the centroid of the bounding box surrounding the structure of interest. Further, the CT image G1 and the MRI image G2 may be aligned with each other by deforming the MRI image G2 non-linearly with respect to the CT image G1 so that the centroid positions g1A to g1C and the centroid positions g2A to g2C match.

Figure 19:
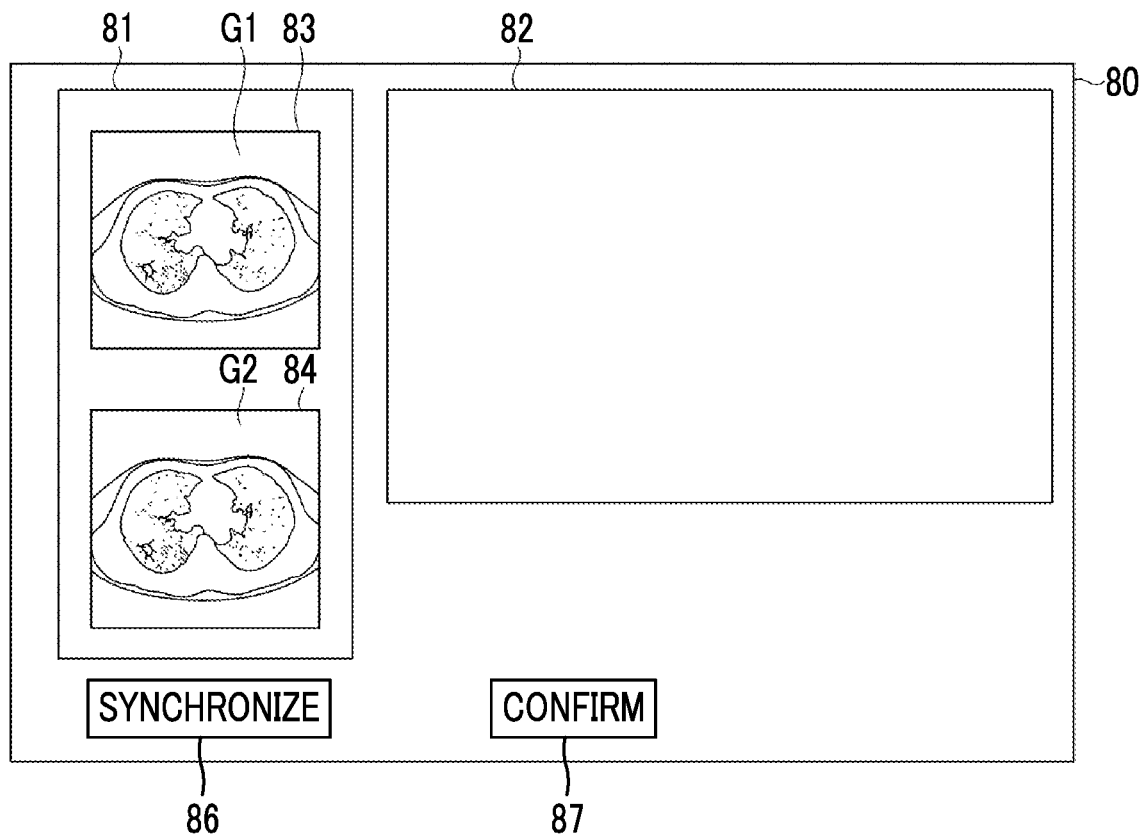
FIG. 19 is a diagram showing a display screen.

The display control unit 26 displays the three-dimensional images G1 and G2 on the display 14. FIG. 19 is a diagram showing a display screen of a three-dimensional image. As shown in FIG. 19, a display screen 80 of the three-dimensional image includes an image display region 81 and a sentence display region 82. The image display region 81 includes a first display region 83 for displaying the CT image G1 and a second display region 84 for displaying the MRI image G2. The tomographic images included in the CT image G1 and the MRI image G2 are displayed in the first display region 83 and the second display region 84. The tomographic image to be displayed can be switched and displayed by selecting either the CT image G1 or the MRI image G2 using the input device 15 and using the scroll wheel or the like provided in the mouse of the input device 15. The positions of the CT image G1 displayed in the first display region 83 and the MRI image G2 displayed in the second display region 84 in the xy direction are aligned by the alignment unit 25. Therefore, the positions on the image of the tomographic plane of the subject included in the CT image G1 and the MRI image G2 displayed in the first display region 83 and the second display region 84 are the same.

Depending on the radiologist, in some cases, it is desired to interpret different tomographic planes in the CT image G1 and the MRI image G2, and in other cases, it is desired to synchronize the displayed tomographic planes. Therefore, in the present embodiment, regarding the position of the displayed tomographic image in the z direction, that is, the position of the tomographic plane, the synchronization and asynchronous of the tomographic planes to be displayed are switched by a synchronization button to be described later.

In the sentence display region 82, comments on findings representing the interpretation results of the CT image G1 and the MRI image G2 by the radiologist are input by using the input device 15.

A synchronization button 86 is displayed below the image display region 81. The synchronization button 86 is for switching between synchronous and asynchronous positions of the tomographic planes of the CT image G1 and the MRI image G2 displayed in the image display region 81. The radiologist displays the tomographic image of the desired tomographic plane in the CT image G1 or the MRI image G2, and selects the synchronization button 86, thereby matching the positions of the tomographic planes of the displayed CT image G1 and MRI image G2. To match the positions of the tomographic planes, the alignment amount for the translation amount in the z direction of the alignment amount by the alignment unit 25 is used. Thereby, the tomographic images displayed on the CT image G1 and the MRI image G2 represent the same tomographic plane. Therefore, by switching the tomographic plane of either the CT image G1 or the MRI image G2, the other tomographic plane can also be switched synchronously. Further, in a case where the synchronization button 86 is selected again after synchronizing the tomographic planes, the synchronization is canceled. This makes it possible to display tomographic images of different tomographic planes on the CT image G1 and the MRI image G2.

A confirmation button 87 is displayed below the sentence display region 82. After inputting the comments on findings, the radiologist can confirm the input content of the comments on findings by selecting the confirmation button 87 using the input device 15.

By the selection of the confirmation button 87 performed by the radiologist, the save control unit 27 transcribes the comments on findings described in the sentence display region 82 to the interpretation report, and saves the interpretation report and the tomographic images of the CT image G1 and the MRI image G2 referred to in the case of generating the interpretation report together in the storage 13.

The communication unit 28 transfers the interpretation report to which the comments on findings described in the sentence display region 82 are transcribed and the tomographic images of the CT image G1 and the MRI image G2 referred to in the case of generating the interpretation report together to the report server 7 via the network I/F 17. The report server 7 saves the interpretation report and the slice image together.

Figure 20:
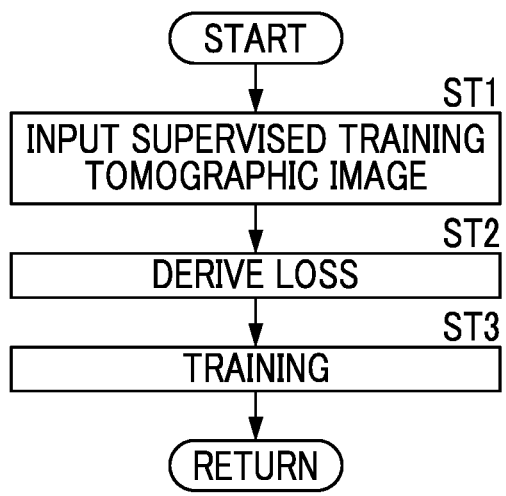
FIG. 20 is a flowchart showing learning processing performed in the present embodiment.

Next, processing performed in the present embodiment will be described. FIG. 20 is a flowchart showing a learning process performed in the present embodiment. It is assumed that a plurality of pieces of supervised training data are acquired from the image server 5 and saved in the storage 13. First, the learning unit 24 inputs a supervised training tomographic image included in the supervised training data to the network 30 (Step ST1), and derives a loss based on the label and the supervised training three-dimensional coordinate information included in the supervised training data and the score and the three-dimensional coordinate information about the structure output from the network 30 (Step ST2).

Then, the learning unit 24 trains the network 30 so that the loss becomes equal to or less than a predetermined threshold value (Step ST3). Thereafter, the process returns to Step ST1, the next supervised training data is acquired from the storage 13, and the processes of Steps ST1 to ST3 are repeated. The processes of Steps ST1 to ST3 may be repeated until the loss becomes equal to or less than a predetermined threshold value, or may be repeated a predetermined number of times. Thereby, the trained derivation model 23A is constructed.

Figure 21:
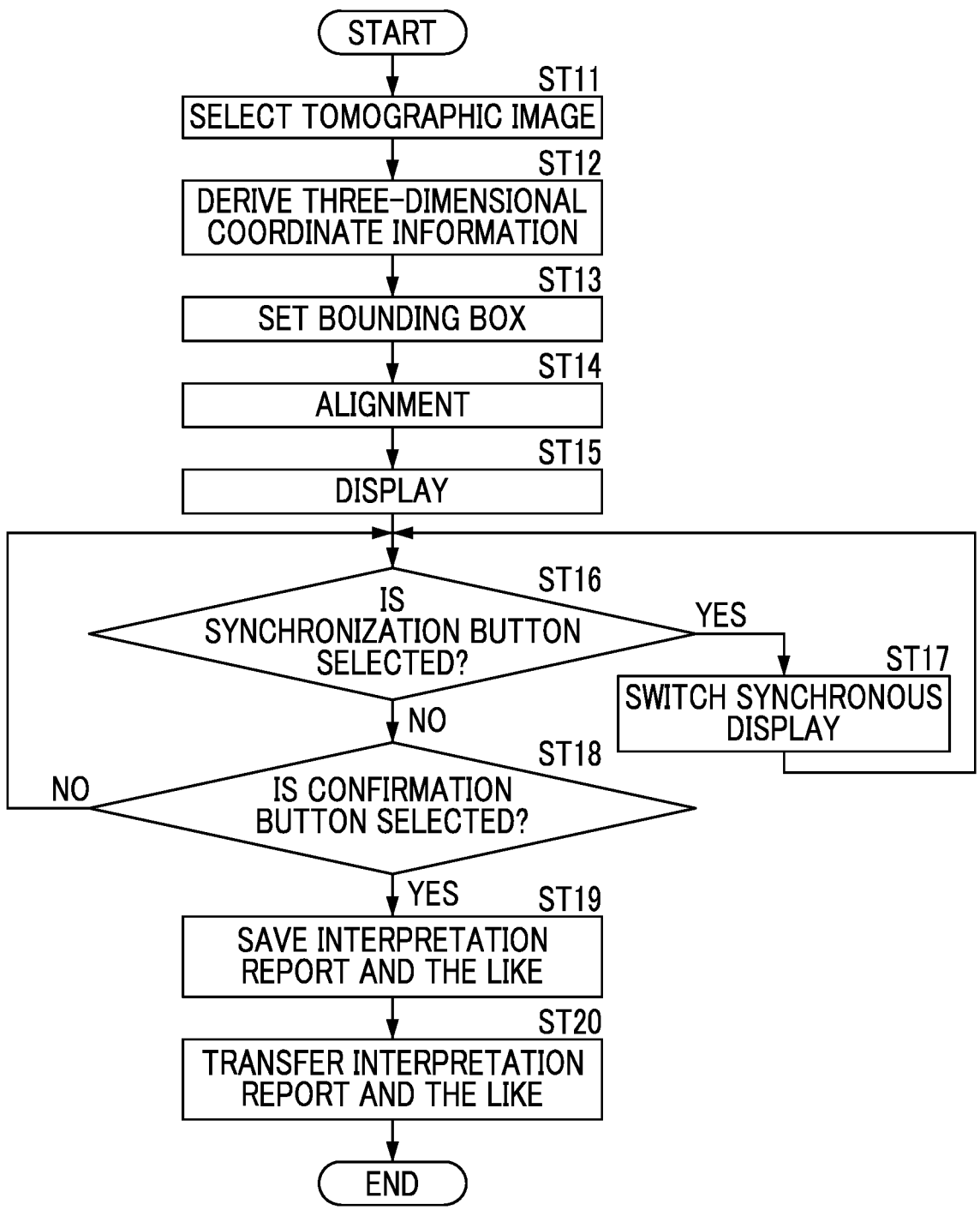
FIG. 21 is a flowchart showing image processing performed in the present embodiment.

Next, image processing performed in the present embodiment will be described. FIG. 21 is a flowchart showing image processing performed in the present embodiment. It is assumed that the CT image G1 and the MRI image G2 to be interpreted are acquired from the image server 5 by the image acquisition unit 21 and are saved in the storage 13. The process is started in a case where an instruction to create an interpretation report is given by the radiologist, and the selection unit 22 selects the tomographic image DGk from the CT image G1 and the MRI image G2 (Step ST11). Next, the derivation unit 23 derives three-dimensional coordinate information that defines a position of a structure included in the tomographic image DGk in the tomographic plane from the tomographic image DGk selected by the selection unit 22, and that defines a position of an end part of the structure outside the tomographic plane in a direction intersecting the tomographic image DGk (Step ST12).

Next, the alignment unit 25 sets a bounding box based on the three-dimensional coordinate information in the CT image G1 and the MRI image G2 (Step ST13), and aligns the CT image G1 and the MRI image G2 using the set bounding box (Step ST14). Next, the display control unit 26 displays the CT image G1 and the MRI image G2 on the display screen 80 (Step ST15). Subsequently, monitoring of whether or not the synchronization button 86 is selected is started (Step ST16). In a case where Step ST16 is affirmative, the positions of CT image G1 and MRI image G2 in the z direction are synchronized to display CT image G1 and MRI image G2 (switching of synchronous display; Step ST17), and the process returns to Step ST16. In this state, the radiologist can interpret the displayed CT image G1 and MRI image G2 and input the comment on findings in the sentence display region 82. In a case where the synchronization button 86 is selected again during the synchronous display, the synchronous display can be switched to the asynchronous display.

In a case where Step ST16 is negative, the display control unit 26 determines whether or not the confirmation button 87 is selected (Step ST18), and in a case where Step ST18 is negative, the process returns to Step ST16. In a case where Step ST18 is affirmative, the save control unit 27 transcribes the comments on findings to the interpretation report for the CT image G1 and the MRI image G2, and saves the interpretation report, the CT image G1, and the MRI image G2 together in the storage 13 (saving of the interpretation report and the like; Step ST19). Then, the communication unit 28 transfers the interpretation report R1, the CT image G1, and the MRI image G2 together to the report server 7 via the network I/F17 (transfer of the interpretation report or the like; Step ST20), and ends the process.

In this way, in the present embodiment, it is configured to derive three-dimensional coordinate information that defines the position of the structure included in the tomographic image DGk in the tomographic plane from the two-dimensional tomographic image DGk selected from the three-dimensional images such as the CT image G1 or the MRI image G2, and that defines the position of the end part of the structure outside the tomographic plane in the direction intersecting the tomographic image DGk. Therefore, the amount of information required to be processed is reduced as compared with the case where the three-dimensional coordinate information of the structure included in the three-dimensional image is derived using the three-dimensional image itself. Thereby, three-dimensional coordinate information can be derived with a small amount of calculation. Therefore, according to the present embodiment, it is possible to efficiently set the three-dimensional coordinates indicating the range of the structure in the three-dimensional image.

Further, in the present embodiment, it is possible to efficiently set the bounding box for the structure included in the three-dimensional image by using the derived three-dimensional coordinate information. Further, by using the set bounding box, it is possible to efficiently align the CT image G1 and the MRI image G2.

Figure 22:
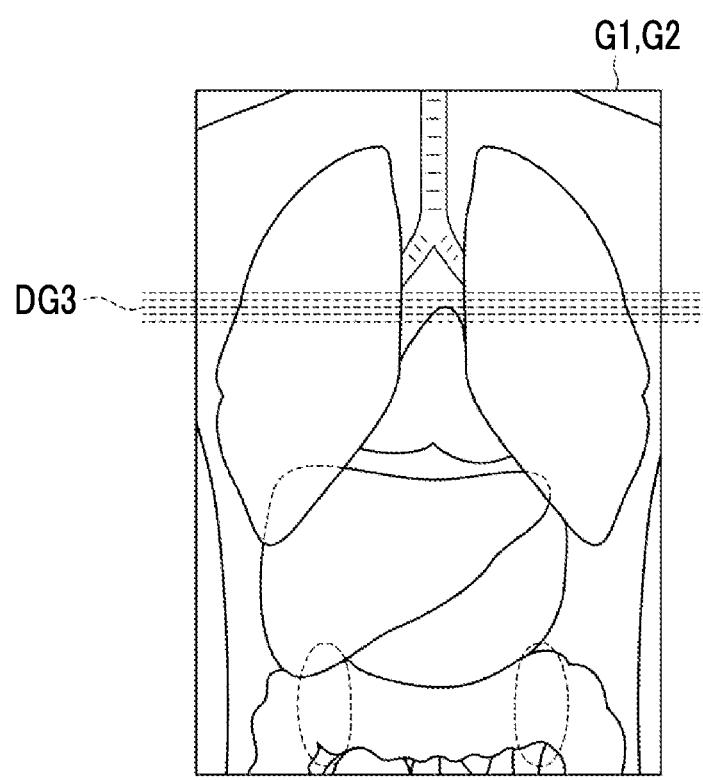
FIG. 22 is a diagram for describing the selection of tomographic images.

In the above embodiment, the derivation unit 23 is configured to derive the three-dimensional coordinate information of the structure included in the tomographic image by inputting one tomographic image, but the present disclosure is not limited thereto. By inputting a plurality of tomographic images as one set into the derivation model 23A, one piece of three-dimensional coordinate information may be derived for a common structure included in each of the plurality of tomographic images. For example, as shown in FIG. 22, by inputting the tomographic image DG3 and a plurality of tomographic images (five in total in FIG. 22) adjacent to the tomographic image DG3 into the derivation model 23A as a set, one piece of three-dimensional coordinate information about the left lung may be derived. That is, by inputting five tomographic images, the three-dimensional coordinates of two points defining one bounding box surrounding the left lung may be derived.

In this case, the derivation model 23A is constructed by machine learning using supervised training data consisting of a plurality of supervised training tomographic images including a common structure, labels for structures common to the plurality of supervised training tomographic images, and supervised training three-dimensional coordinate information about the structure. Thereby, in a case where a set of a plurality of tomographic images is input, it is possible to construct the derivation model 23A that outputs three-dimensional coordinate information defining the end parts of a common structure included in the plurality of tomographic images.

In this case, the number of tomographic images input to the derivation model 23A may be any number, but it is smaller than the number of all tomographic images constituting the three-dimensional image. Thereby, three-dimensional coordinate information can be derived with a smaller amount of calculation than in the case where the three-dimensional image itself is used.

In addition, in the above embodiment, the derivation of the three-dimensional coordinate information from the CT image G1 and the derivation of the three-dimensional coordinate information from the MRI image G2 may be performed by different derivation models. For example, as a derivation model for deriving three-dimensional coordinate information from CT image G1, a model for deriving three-dimensional coordinate information by inputting one tomographic image may be used, and as a derivation model for deriving three-dimensional coordinate information from MRI image G2, a model for deriving one piece of three-dimensional coordinate information about a structure common to a plurality of tomographic images by inputting a plurality of tomographic images may be used.

Further, in the above embodiment, the same number of tomographic images are selected from the CT image G1 and the MRI image G2, respectively, but the present disclosure is not limited thereto. A different number of tomographic images may be selected from each of the CT image G1 and the MRI image G2. For example, only one tomographic image may be selected from either the CT image G1 or the MRI image G2. Here, assuming that only one tomographic image is selected from the CT image G1, the bounding box surrounding the structure included in the selected one tomographic image can be set in the CT image G1 using the selected one tomographic image. On the other hand, for the MRI image G2, a bounding box surrounding the structure included in each of the plurality of tomographic images can be set in the MRI image G2 as in the above embodiment. Therefore, for the MRI image G2, the bounding box can be set by deriving the three-dimensional coordinate information for all the structures including the structure from which the three-dimensional coordinate information is derived in the CT image G1. Therefore, even though different numbers of tomographic images are selected for the CT image G1 and the MRI image G2, the CT image G1 and the MRI image G2 can be aligned. Therefore, the CT image G1 and the MRI image G2 can be aligned with a smaller amount of calculation.

Further, in the above embodiment, the selection unit 22 selects a tomographic image from the CT image G1 and the MRI image G2, but the present disclosure is not limited thereto. The display control unit 26 displays the CT image G1 and the MRI image G2 on the display 14, and receives the selection of the desired tomographic plane by the operator from the displayed CT image G1 and MRI image G2, such that the selection unit 22 may select a tomographic image.

Further, in the above embodiment, the derivation unit 23 derives the two vertices at the farthest positions among the eight vertices in the bounding box as three-dimensional coordinate information, but the present disclosure is not limited thereto. The derivation unit 23 may derive a plurality of vertices capable of defining a bounding box other than the two vertices at the farthest positions as three-dimensional coordinate information. For example, all three-dimensional coordinates of the eight vertices defining the bounding box may be derived as three-dimensional coordinate information. In this case, the derivation model 23A may be constructed so that in a case where the tomographic image is input, the three-dimensional coordinate information for a plurality of predetermined vertices in the bounding box surrounding the structure is output. Learning of such a derivation model 23A may be performed using supervised training data including supervised training three-dimensional coordinate information for a plurality of predetermined vertices in the bounding box.

Further, in the above embodiment, the derivation unit 23 may derive information on the orientation of the structure. In this case, the derivation model 23A may be constructed so that in a case where a tomographic image is input, information on the orientation of the structure is output in addition to the three-dimensional coordinate information defining the end part of the structure by performing machine learning using supervised training data including information on the orientation of the structure.

In a case where the derivation model 23A is constructed in this way, the following process can be performed. That is, for example, in one examination for capturing an MRI image, an MRI image in the axial direction and an MRI image in the sagittal direction may be mixed. In such a case, the three-dimensional coordinate information of the structure is determined using both images. That is, provisional three-dimensional coordinate information and the orientation of the structure are derived by using the derivation model 23A constructed so as to output the information on the orientation of the structure from the tomographic images of the MRI image in the axial direction and the MRI image in the sagittal direction. Here, the MRI images in both directions include information indicating the relationship between the relative position and orientation between cross sections of an axial image and a sagittal image in accessory information (for example, DICOM information) attached to the image. Therefore, by integrating the provisional three-dimensional coordinate information based on the provisional three-dimensional coordinate information and orientation derived by the derivation model 23A and the information indicating the relationship between the relative position and orientation between the cross sections of the axial image and the sagittal image, it is possible to obtain the three-dimensional coordinate information defining the end part of the structure more accurately.

Further, in the above embodiment, three-dimensional coordinate information about the structure included in the CT image G1 and the MRI image G2 is derived for the alignment of the CT image G1 and the MRI image G2 acquired by different imaging apparatuses, but the image to be processed is not limited to these. For example, the technique of the present disclosure can also be applied in the case of aligning the latest three-dimensional image (referred to as a target three-dimensional image) of the same patient with the past three-dimensional image acquired by capturing an image in the past.

In this case, the selection unit 22 may select at least one tomographic image from each of the target three-dimensional image and the past three-dimensional image, and the derivation unit 23 may derive the three-dimensional coordinate information defining the end part of the structure in the direction intersecting the selected tomographic image in each of the target three-dimensional image and the past three-dimensional image. The target three-dimensional image and the past three-dimensional image may be acquired by the same imaging apparatus, or may be acquired by different imaging apparatuses. For example, the target three-dimensional image may be a CT image, and the past three-dimensional image may be an MRI image. Thereby, even in a case where follow-up observation for the same patient is performed, the alignment of the tomographic plane between the target three-dimensional image and the past three-dimensional image can be efficiently performed.

Further, in the present embodiment, for example, in the case of capturing an image using a contrast medium, the CT image before contrast enhancement and the CT image after contrast enhancement can be the target of alignment. In this case, the selection unit 22 may select at least one tomographic image from each of the CT image before contrast enhancement and the CT image after contrast enhancement, and the derivation unit 23 may derive the three-dimensional coordinate information defining the end part of the structure in the direction intersecting the selected tomographic image in each of the CT image before contrast enhancement and the CT image after contrast enhancement. Thereby, even in the case of observing the patient's condition before and after contrast enhancement, it is possible to efficiently align the displayed tomographic planes between the CT image before contrast enhancement and the CT image after contrast enhancement.

Further, in the above embodiment, the alignment is performed in the x direction, the y direction, and the z direction, but the present disclosure is not limited thereto. In the x direction and the y direction, the CT image G1 and the MRI image G2 are generally aligned at the time of imaging. Therefore, the alignment may be performed only in the z direction.

Further, in the above embodiment, in order to align a plurality of three-dimensional images, the three-dimensional coordinate information defining the end part of the structure in the direction intersecting the selected tomographic image is derived using the tomographic image selected from each of the plurality of tomographic images, but the present disclosure is not limited thereto. The three-dimensional coordinate information derived by the present embodiment can also be used in the case of performing the process of extracting the target structure from one three-dimensional image.

For example, in a case where a process of extracting a liver from a three-dimensional image is performed, three-dimensional coordinate information defining the end part of the liver is derived according to the present embodiment before the extraction process. Then, a bounding box surrounding the liver is set based on the derived three-dimensional coordinate information. Next, the process of extracting the liver is performed in the vicinity of the bounding box. Here, the amount of calculation is smaller in a case where the extraction process is performed using only the image near the bounding box than in a case where the extraction process is performed on the entire three-dimensional image. Therefore, in the case of performing the process of extracting the structure from the three-dimensional image, by setting the bounding box using the three-dimensional coordinate information derived by the present embodiment, extraction of a desired structure from a three-dimensional image can be efficiently performed with a small amount of calculation.

Further, in the above embodiment, the tomographic image of the axial cross section is selected as the tomographic image to be selected from the three-dimensional images, but the present disclosure is not limited thereto. A tomographic image of a coronal cross section or a sagittal cross section may be selected. In this case, the derivation model 23A in the derivation unit 23 may be constructed so as to derive three-dimensional coordinate information defining the end part of the structure in the direction intersecting the coronal cross section or the sagittal cross section in the three-dimensional image by inputting the tomographic image of the coronal cross section or the sagittal cross section. In this case, supervised training data including a supervised training tomographic image of a coronal cross section or a sagittal cross section is used for training the derivation model 23A.

Further, in the above embodiment, one tomographic image may not include the entire tomographic plane of the structure, and the structure may be cut off in the tomographic image. In such a case, in addition to the direction in which the tomographic image intersects, the three-dimensional coordinate information defining the end part of the structure in the tomographic plane represented by the tomographic image may be derived.

Further, in the above embodiment, for example, as hardware structures of processing units that execute various kinds of processing, such as the image acquisition unit 21, the selection unit 22, the derivation unit 23, the learning unit 24, the alignment unit 25, the display control unit 26, the save control unit 27, and the communication unit 28, various processors shown below can be used. As described above, the various processors include a programmable logic device (PLD) as a processor of which the circuit configuration can be changed after manufacture, such as a field programmable gate array (FPGA), a dedicated electrical circuit as a processor having a dedicated circuit configuration for executing specific processing such as an application specific integrated circuit (ASIC), and the like, in addition to the CPU as a general-purpose processor that functions as various processing units by executing software (programs).

One processing unit may be configured by one of the various processors, or may be configured by a combination of the same or different kinds of two or more processors (for example, a combination of a plurality of FPGAs or a combination of the CPU and the FPGA). In addition, a plurality of processing units may be configured by one processor.

As an example where a plurality of processing units are configured by one processor, first, there is a form in which one processor is configured by a combination of one or more CPUs and software as typified by a computer, such as a client or a server, and this processor functions as a plurality of processing units. Second, there is a form in which a processor for realizing the function of the entire system including a plurality of processing units via one integrated circuit (IC) chip as typified by a system on chip (SoC) or the like is used. In this way, various processing units are configured by one or more of the above-described various processors as hardware structures.

Furthermore, as the hardware structure of the various processors, more specifically, an electrical circuit (circuitry) in which circuit elements such as semiconductor elements are combined can be used.

What is claimed is:

1. An image processing apparatus comprising at least one processor, wherein the processor is configured to:
   select a tomographic image from a plurality of tomographic images, wherein the tomographic image has a tomographic plane which intersects a structure to be detected; and
   derive, based on a derivation model constructed by performing machine learning using supervised training data, three-dimensional coordinate information that defines positions of the structure intersecting the tomographic plane, the positions of the structure include a position of an end part of the structure outside the tomographic plane in a direction intersecting the tomographic image, wherein
      the three-dimensional coordinate information includes three-dimensional coordinates of a plurality of vertices defining a rectangular cuboid surrounding the structure, and
      the plurality of vertices includes only two vertices at the farthest positions among the vertices defining the rectangular cuboid for each rectangular cuboid surrounding the structure.

2. The image processing apparatus according to claim 1, wherein the processor is configured to select a plurality of tomographic images from a computed tomography (CT) image and a magnetic resonance imaging (MRI) image at predetermined intervals, and the plurality of tomographic images include the structure from a three-dimensional image.

3. The image processing apparatus according to claim 1, wherein the processor is configured to derive the three-dimensional coordinate information by deriving provisional three-dimensional coordinate information about the structure from each of a plurality of tomographic images including a common structure, and integrating the provisional three-dimensional coordinate information.

4. The image processing apparatus according to claim 3, wherein the processor is configured to derive the three-dimensional coordinate information by converting the provisional three-dimensional coordinate information for each of the plurality of tomographic images into a common coordinate system, and integrating the converted provisional three-dimensional coordinate information.

5. The image processing apparatus according to claim 3, wherein the processor is configured to derive the three-dimensional coordinate information by integrating the provisional three-dimensional coordinate information closer to an upper end or a lower end of the same structure with high priority with respect to the provisional three-dimensional coordinate information derived for the tomographic image including the upper end or the lower end.

6. The image processing apparatus according to claim 1, wherein the processor is configured to
   acquire a first three-dimensional image and a second three-dimensional image each including a plurality of tomographic images and a common structure,
   derive first three-dimensional coordinate information about the structure included in the first three-dimensional image and second three-dimensional coordinate information about the structure included in the second three-dimensional image, and
   align the first three-dimensional image and the second three-dimensional image at least in the direction intersecting the tomographic image by using the first three-dimensional coordinate information and the second three-dimensional coordinate information to align the common structure included in each of the first three-dimensional image and the second three-dimensional image at least in the direction intersecting the tomographic image.

7. The image processing apparatus according to claim 6, wherein the first three-dimensional image and the second three-dimensional image are three-dimensional images of the same subject imaged with different imaging apparatuses.

8. The image processing apparatus according to claim 6, wherein the first three-dimensional image and the second three-dimensional image are three-dimensional images of the same subject imaged at different imaging times.

9. The image processing apparatus according to claim 6, wherein the processor is configured to derive the first and second three-dimensional coordinate information for each of the first and second three-dimensional images by different methods.

10. The image processing apparatus according to claim 1, further comprising:
   a derivation model trained using supervised training data to output the three-dimensional coordinate information that, in a case where the tomographic image is input, defines the positions of the structure included in the input tomographic image in the tomographic plane, and that defines the position of the end part of the structure outside the tomographic plane in the direction intersecting the tomographic image.

11. A learning apparatus comprising at least one processor,
wherein the processor is configured to
select a tomographic image from a plurality of tomographic images, wherein the tomographic image has a tomographic plane which intersects a structure to be detected; and
derive, based on a derivation model constructed by performing machine learning using supervised training data, three-dimensional coordinate information that defines positions of the structure intersecting the tomographic plane, the positions of the structure include a position of an end part of the structure outside the tomographic plane in a direction intersecting the tomographic image, wherein
the three-dimensional coordinate information includes three-dimensional coordinates of a plurality of vertices defining a rectangular cuboid surrounding the structure, and
the plurality of vertices includes only two vertices at the farthest positions among the vertices defining the rectangular cuboid for each rectangular cuboid surrounding the structure.

12. The learning apparatus according to claim 11,
wherein the supervised training data includes a supervised training tomographic image and supervised training three-dimensional coordinate information that defines positions of the structure included in the supervised training tomographic image in the tomographic plane, and that defines the position of the end part of the structure outside the tomographic plane in the direction intersecting the supervised training tomographic image.

13. An image processing method comprising deriving three-dimensional coordinate information that defines a position of a structure in a tomographic plane from a tomographic image including the structure, and that defines a position of an end part of the structure outside the tomographic plane in a direction intersecting the tomographic image, the method comprising:
selecting a tomographic image from a plurality of tomographic images, wherein the tomographic image has the tomographic plane which intersects the structure to be detected; and
deriving, based on a derivation model constructed by performing machine learning using supervised training data, three-dimensional coordinate information that defines positions of the structure intersecting the tomographic plane, the positions of the structure include the position of the end part of the structure outside the tomographic plane in a direction intersecting the tomographic image, wherein
the three-dimensional coordinate information includes three-dimensional coordinates of a plurality of vertices defining a rectangular cuboid surrounding the structure, and
the plurality of vertices includes only two vertices at the farthest positions among the vertices defining the rectangular cuboid for each rectangular cuboid surrounding the structure.

14. A learning method comprising constructing a derivation model by performing machine learning using supervised training data, the derivation model outputting three-dimensional coordinate information that, in a case where a tomographic image is input, defines a position of a structure included in the input tomographic image in a tomographic plane, and that defines a position of an end part of the structure outside the tomographic plane in a direction intersecting the tomographic image, the method comprising:
performing machine learning using the supervised training data, the derivation model;
selecting a tomographic image from a plurality of tomographic images, wherein the tomographic image has the tomographic plane which intersects the structure to be detected; and
deriving, based on the derivation model constructed by performing machine learning using supervised training data, three-dimensional coordinate information that defines positions of the structure intersecting the tomographic plane, the positions of the structure include the position of the end part of the structure outside the tomographic plane in a direction intersecting the tomographic image, wherein
the three-dimensional coordinate information includes three-dimensional coordinates of a plurality of vertices defining a rectangular cuboid surrounding the structure, and
the plurality of vertices includes only two vertices at the farthest positions among the vertices defining the rectangular cuboid for each rectangular cuboid surrounding the structure.

15. A non-transitory computer-readable storage medium that stores an image processing program causing a computer to execute a procedure of deriving three-dimensional coordinate information that defines a position of a structure in a tomographic plane from a tomographic image including the structure, and that defines a position of an end part of the structure outside the tomographic plane in a direction intersecting the tomographic image, the procedure comprising:
selecting a tomographic image from a plurality of tomographic images, wherein the tomographic image has the tomographic plane which intersects the structure to be detected; and
deriving, based on a derivation model constructed by performing machine learning using supervised training data, three-dimensional coordinate information that defines positions of the structure intersecting the tomographic plane, the positions of the structure include the position of the end part of the structure outside the tomographic plane in a direction intersecting the tomographic image, wherein
the three-dimensional coordinate information includes three-dimensional coordinates of a plurality of vertices defining a rectangular cuboid surrounding the structure, and
the plurality of vertices includes only two vertices at the farthest positions among the vertices defining the rectangular cuboid for each rectangular cuboid surrounding the structure.

16. A non-transitory computer-readable storage medium that stores a learning program causing a computer to execute a procedure of constructing a derivation model by performing machine learning using supervised training data, the derivation model outputting three-dimensional coordinate information that, in a case where a tomographic image is input, defines a position of a structure included in the input tomographic image in a tomographic plane, and that defines a position of an end part of the structure outside the tomographic plane in a direction intersecting the tomographic image, the procedure comprising:

performing machine learning using the supervised training data, the derivation model;

selecting a tomographic image from a plurality of tomographic images, wherein the tomographic image has the tomographic plane which intersects the structure to be detected; and deriving, based on the derivation model constructed by performing machine learning using supervised training data, three-dimensional coordinate information that defines positions of the structure intersecting the tomographic plane, the positions of the structure include the position of the end part of the structure outside the tomographic plane in a direction intersecting the tomographic image, wherein the three-dimensional coordinate information includes three-dimensional coordinates of a plurality of vertices defining a rectangular cuboid surrounding the structure, and the plurality of vertices includes only two vertices at the farthest positions among the vertices defining the rectangular cuboid for each rectangular cuboid surrounding the structure.

\* \* \* \* \*